(12) United States Patent
Korlach et al.

(10) Patent No.: US 9,063,156 B2
(45) Date of Patent: Jun. 23, 2015

(54) REAL-TIME ANALYTICAL METHODS AND SYSTEMS

(75) Inventors: Jonas Korlach, Newark, CA (US); Stephen Turner, Menlo Park, CA (US); Benjamin Flusberg, Palo Alto, CA (US); Mark Chaisson, San Francisco, CA (US); Eric Schadt, Palo Alto, CA (US); Jeffrey Wegener, Cupertino, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 12/814,075

(22) Filed: Jun. 11, 2010

(65) Prior Publication Data

US 2010/0323912 A1    Dec. 23, 2010

Related U.S. Application Data

(63) Continuation-in-part of application No. 12/635,618, filed on Dec. 10, 2009.

(60) Provisional application No. 61/186,661, filed on Jun. 12, 2009.

(51) Int. Cl.
| | | |
|---|---|---|
| C12Q 1/68 | (2006.01) | |
| G01N 33/53 | (2006.01) | |
| G01N 33/68 | (2006.01) | |
| G01N 33/542 | (2006.01) | |
| G01N 33/543 | (2006.01) | |

(52) U.S. Cl.
CPC .......... *G01N 33/6875* (2013.01); *C12Q 1/6825* (2013.01); *C12Q 1/6827* (2013.01); *C12Q 1/6869* (2013.01); *G01N 33/542* (2013.01); *G01N 33/54306* (2013.01); *G01N 33/54373* (2013.01)

(58) Field of Classification Search
CPC ............... C12Q 1/6825; C12Q 1/6869; G01N 33/54306; G01N 33/54373; G01N 33/6818; G01N 2400/00
See application file for complete search history.

(56) References Cited

U.S. PATENT DOCUMENTS

| | | | |
|---|---|---|---|
| 6,066,462 A | 5/2000 | Goueli | |
| 6,255,083 B1 | 7/2001 | Williams | |
| 6,344,316 B1* | 2/2002 | Lockhart et al. ................... | 506/9 |
| 6,787,308 B2 | 9/2004 | Balasubramanian et al. | |
| 6,917,726 B2 | 7/2005 | Levene et al. | |
| 7,056,661 B2 | 6/2006 | Korlach et al. | |
| 7,170,050 B2 | 1/2007 | Turner et al. | |
| 7,292,742 B2 | 11/2007 | Levene et al. | |
| 7,304,146 B2 | 12/2007 | Lee et al. | |
| 7,313,308 B2 | 12/2007 | Turner et al. | |
| 7,315,019 B2 | 1/2008 | Turner et al. | |
| 7,993,840 B2 | 8/2011 | Alexandre et al. | |
| 8,460,879 B2 | 6/2013 | Walt et al. | |
| 2003/0235828 A1* | 12/2003 | Gillibolian et al. ............... | 435/6 |
| 2004/0048287 A1* | 3/2004 | Smith et al. ...................... | 435/6 |
| 2006/0057569 A1* | 3/2006 | Charle .............. | 435/6 |
| 2006/0063264 A1* | 3/2006 | Turner et al. ....................... | 436/8 |
| 2008/0108128 A1 | 5/2008 | Eidne et al. | |
| 2009/0142772 A1 | 6/2009 | Lau et al. | |
| 2009/0159812 A1 | 6/2009 | Livingston | |
| 2010/0022022 A1 | 1/2010 | Graham et al. | |
| 2011/0065597 A1 | 3/2011 | Williams et al. | |
| 2012/0129723 A1 | 5/2012 | Notcovich et al. | |

FOREIGN PATENT DOCUMENTS

| | | |
|---|---|---|
| WO | WO 2006/125012 A2 | 11/2006 |
| WO | WO 2009/039639 A1 | 4/2009 |

OTHER PUBLICATIONS

Lee et al. Biochemistry (1997) 36: 2701-2708.*
Berger et al. Nature Biotechnology (2006) 24(11): 1429-1435.*
Xu et al. Bioorganic & Medicinal Chemistry (2006) 14: 2660-2673.*
Kajihara et al. Nature Methods (2006) 3(11): 923-929.*
Brodie et al. Journal of Molecular Endocrinology (2005) 34: 603-615.*
Korn et al. Nucleic Acids Research (2003) 31(16): e89.*
Berger, et al., Nat. Biotech. 24:1429-1435 (2006).
Bodenreider, et al., Anal. Biochem, 395(2):195-204 (2009).
Burk, at al., Biochemistry 40:8756-8764 (2001).
Cwirla, et al., Proc. Nat. Acad. Sci. USA 87:6378-6382 (1990).
Eid et al., Science 323:133-138 (2009).
Erlich, et al., Genome Research 19:1243-1253 (2009).
Glass, et al., Adv. Funct. Mat. 13:569-575 (2003).
Glass, et al., Nanotechnology 14(10):1153-1160 (2003).
Lengsfeld, et al., J. Pharm, Sci. 91(7):1581-1589 (2002).
Levene et al., Science 299 (5607):682-686 (2003).
Liu, et al., Int. J. Peptide Prot. Res, 35(2):95-98 (1990).
Mutter, et al., Helvetica Chimica Acta 67:2009-2016 (1984).
Oka, at al., Bioorg. Med. Chem. Lett. 14:3241-3244 (2004).
Park, P.J., Nat. Rev. Genet. 10:669-680 (2009).
Ren, et al., Science 290:2306-2309 (2000).

(Continued)

*Primary Examiner* — Angela M Bertagna
(74) *Attorney, Agent, or Firm* — Deana A. Arnold

(57) ABSTRACT

The present invention is generally directed to compositions, methods, and systems for performing single-molecule, real-time analysis of a variety of different biological reactions, and for determining various characteristics of the different biological reactions. The ability to analyze such reactions provides an opportunity to study those reactions as well as to potentially identify factors and/or approaches for impacting such reactions, e.g., to stimulate, enhance, or inhibit such reactions.

15 Claims, 7 Drawing Sheets

(56) References Cited

OTHER PUBLICATIONS

Salmon, et al., Proc. Nat. Acad, Sci. USA 90:11708-11712 (1993).
Samiee, et al., Biophysical Journal 88:2145-2153 (2005).
Tiffany, et al., Clinical Chemistry 17(8):715-720 (1971).
White, et al., J. Am. Chem. Soc. 129:11766-11775 (2007).
Wilson-Lingardo, et al., J. Med. Chem. 39(14):2720-2726 (1996).
Banerjee et al. "Structure of a repair enzyme interrogating undamaged DNA elucidates recognition of damaged DNA" Nature (2005) 434:612-618.
Blainey et al. "A base-excision DNA-repair protein finds intrahelical lesion bases by fast sliding in contact with DNA" PNAS (2006) 103(15):5752-5757.
Finkel et al. "Oxidants, oxidative stress and the biology ageing" Nature (2000) 408:239-247.
Fodor et al. "Light-directed, spatially addressable parallel chemical synthesis" Science (1991) 251:767-773.
Fromme et al. "Base excision repair" Adv Protein Chem (2004) 69:1-41.
Goren at al. "Chromatin profiling by directly sequencing small quantities of immunoprecipitated DNA" Nature Meth (2010) 7(1):47-49 and online methods.
Hamm et al. "Substrate specificity of Fpg (MutM) and hOGG1, Two repair glycosylases" JACS (2007) 129 (25):7724-7725.
Hsu et al. "Error-prone replication of oxidatively damagedDNA by a high-fidelity DNA polymerase" Nature (2004) 431:217-221.
Klungland et al., "Oxidative damage to purines in DNA: role of mammalian OGG1" DNA Repair (Amst) (2007) 6 (4):481-488.
Lindahl et al., "Instability and decay of the primary structure of DNA" Nature (1993) 362:709-715.
McCullough et al., "Initiation of base excision repair: glycosylase mechanisms and structures" Ann Rev Biochem (1999)68:255-285.
Radicella et al., "Cloning and characterization of hOGG1, a human homolog of the OGG1 gene of *Saccharomyces cerevisiae*" PNAS (1997) 94:8010-8015.
Vidal et al., "Mechanism of stimulation of the DNA glycosylase activity of gOGG1 by the major human AP endonuclease: bypass of the AP lyase activity step" Nuc Acids Res (2001) 29(6):1285-1292.
Ibach et al., "Sequencing Single DNA Molecules in Real Time," Angewandte Chemie International Edition (2009) 48 (26):4683-4685.
International Search Report and Written Opinion dated May 13, 2011 for related case PCT/US2010/001690.

* cited by examiner

C.
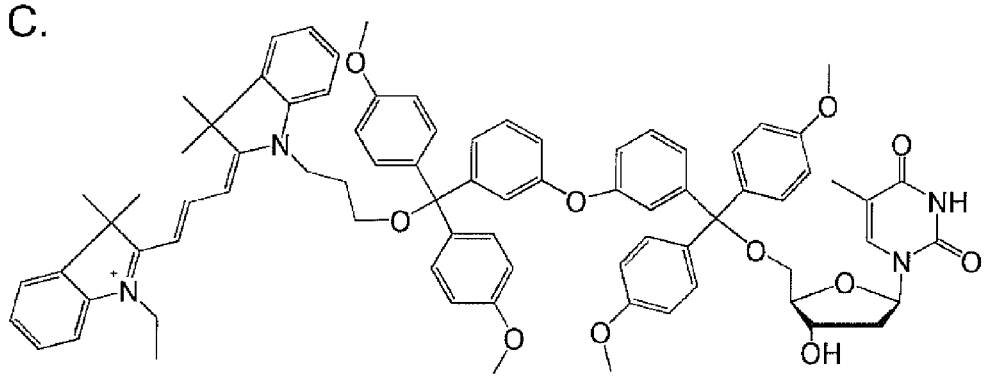
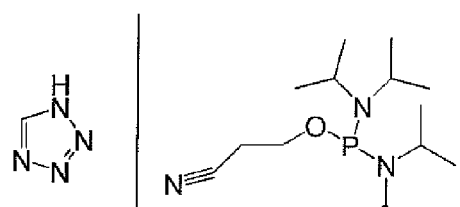
D.
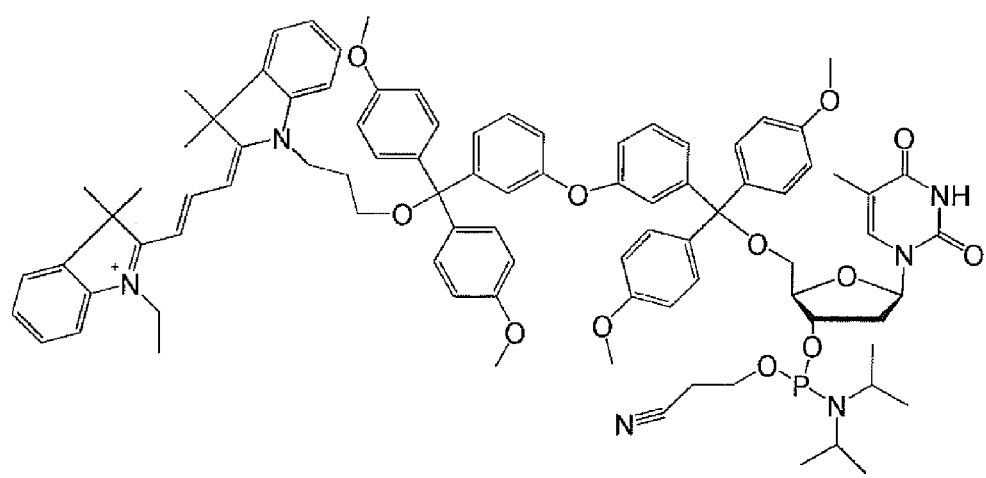
Figure 3, cont.

REAL-TIME ANALYTICAL METHODS AND SYSTEMS

CROSS-REFERENCE TO RELATED APPLICATIONS

This application claims the benefit of U.S. Ser. No. 61/186,661, filed Jun. 12, 2009; and is a continuation-in-part application of U.S. Ser. No. 12/635,618, filed Dec. 10, 2009, the disclosures of which are incorporated herein by reference in their entireties for all purposes.

STATEMENT REGARDING FEDERALLY SPONSORED RESEARCH

Not Applicable.

BACKGROUND OF THE INVENTION

Assays for analysis of biological processes are exploited for a variety of desired applications. For example, monitoring the activity of key biological pathways can lead to a better understanding of the functioning of those systems as well as those factors that might disrupt the proper functioning of those systems. In fact, various different disease states caused by operation or disruption of specific biological pathways are the focus of much medical research. By understanding these pathways, one can model approaches for affecting them to prevent the onset of the disease or mitigate its effects once manifested.

A stereotypical example of the exploitation of biological process monitoring is in the area of pharmaceutical research and development. In particular, therapeutically relevant biological pathways, or individual steps or subsets of individual steps in those pathways, are often reproduced or modeled in in vitro systems to facilitate analysis. By observing the progress of these steps or whole pathways in the presence and absence of potential therapeutic compositions, e.g., pharmaceutical compounds or other materials, one can identify the ability of those compositions to affect the in vitro system, and potentially beneficially affect an organism in which the pathway is functioning in a detrimental way. By way of specific example, a variety of kinase enzymes have been identified as key pathway components in a number of therapeutically relevant biological pathways, as they will often phosphorylate different substrate proteins upon the binding of different effector compounds, e.g., cytokines, to receptors on biological proteins, e.g., cell surface receptors. By modeling the kinase reaction system in vitro and testing it against libraries of potential pharmaceutical candidates, one can identify the compounds which best inhibit or enhance the reaction in question.

Typically, modeled biological systems rely on bulk reactions that ascertain general trends of biological reactions and provide indications of how such bulk systems react to different effectors. While such systems are useful as models of bulk reactions in vivo, a substantial amount of information is lost in the averaging of these bulk reaction results. In particular, the activity of and effects on individual molecular complexes cannot generally be teased out of such bulk data collection strategies.

Single-molecule real-time analysis of nucleic acid synthesis has been shown to provide powerful advantages over nucleic acid synthesis monitoring that is commonly exploited in sequencing processes. In particular, by concurrently monitoring the synthesis process of nucleic acid polymerases as they work in replicating nucleic acids, one gains advantages of a system that has been perfected over millions of years of evolution. In particular, the natural DNA synthesis processes provide the ability to replicate whole genomes in extremely short periods of time, and do so with an extremely high level of fidelity to the underlying template being replicated.

BRIEF SUMMARY OF THE INVENTION

The present invention is generally directed to compositions, methods, and systems for performing single-molecule, real-time analysis of a variety of different biological reactions. The ability to analyze such reactions provides an opportunity to study those reactions as well as to potentially identify factors and/or approaches for impacting such reactions, e.g., to either enhance or inhibit such reactions.

In certain aspects, methods of detecting binding between a first binding partner and a second binding partner are provided herein. In certain embodiments, such methods comprise immobilizing a single molecule of the first binding partner at a reaction site on a substrate that is optically resolvable from other reaction sites on the substrate, exposing the single molecule of the first binding partner to a reaction mixture comprising the second binding partner, and monitoring the reaction site for retention of the second binding partner, thereby detecting binding between the first binding partner and the second binding partner. In some cases, the first binding partner is a receptor and the second binding partner is a ligand for the receptor. In other cases, the first binding partner is a nucleic acid and the second binding partner is selected from the group consisting of a transcription factor, a histone, an antibody, a modification-binding agent, an RNA, an enzyme, a nucleic acid binding protein, and a nucleic acid binding agent. In preferred embodiments, at least one of the binding partners comprises a detectable label, e.g., a fluorophore; and in some such embodiments both binding partners comprise interactive labels, e.g., FRET labels. In certain embodiments, at least one binding partner undergoes a conformational change upon binding that changes its intrinsic fluorescence, and this change in intrinsic fluorescence is detectable and therefore indicative of a binding event. Optionally, a reaction mixture can comprise an agent that alters binding between the first binding partner and the second binding partner relative to binding in the absence of the agent. Optionally, binding can be monitored under different reaction conditions to generate binding data or results for the different reaction conditions. In specific embodiments, the first binding partner is a product of a reaction taking place at the reaction site, e.g., a nucleic acid product of a template-directed synthesis reaction, e.g., catalyzed by a polymerase enzyme.

In some embodiments, methods to detect binding between binding partners further comprise determining a consensus binding site for one of the binding partners. For example, performing multiple template-directed synthesis reactions on a set of single-stranded nucleic acid templates can be carried out in the presence of a binding partner for which a consensus sequence is to be determined. Each synthesis reaction is localized at a different optically resolvable reaction site on a substrate, and during generation of a plurality of nucleic acid products, incorporation of differentially labeled nucleotides into the plurality of nucleic acid products is monitored and the sequence of nucleotide incorporations is used to determine a set of nucleotide sequences for the nucleic acid products. Binding of the binding partner to a subset of the nucleic acid products is detected, and a nucleotide sequence common to the subset is identified, the common sequence being the consensus binding site of the binding partner.

In other aspects, methods for identifying an abundance of one or more binding agents in a reaction mixture are provided herein. In some embodiments, these methods include providing a set of immobilized targets comprising known binding sites, wherein each immobilized target in the set is bound to a different reaction site in an array; introducing a reaction mixture to the array, wherein the reaction mixture comprises binding agents of unknown abundance; and monitoring binding of the binding agents to the targets, wherein an amount of binding of the binding agents to the targets is indicative of the abundance of the binding agents, thereby identifying an abundance of the binding agents in the reaction mixture. The array is preferably an array of individual optical confinements, e.g., an array of zero mode waveguides. The binding agents include, but are not limited to transcription factors, polymerases, reverse transcriptases, histones, nucleases, restriction enzymes, groove binders, intercalators, antibodies, antigens, ligands, substrates, modification-binding agents, and nucleic acid binding proteins, and nucleic acid binding agents. The binding agents can be obtained from a biological sample, e.g., a cell lysate, bodily fluids or excrement, tissue of a particular developmental stage, tissue of a particular disease state, a sample comprising an unknown microorganism, and a contaminated environmental sample. In certain embodiments, the reaction mixture comprises binding agents of unknown identity, and the monitoring provides identification of at least a portion of the binding agents in the reaction mixture. In certain preferred embodiments, the binding agents are differentially labeled, and the association of a first binding agent with one of the targets on the array results in a detectable signal, the emission spectrum of which identifies the first binding agent.

In further embodiments, a plurality of the first binding agent associates with a plurality of the one target resulting in a plurality of detectable signals, each of which corresponds to the first binding agent, and an abundance of the plurality of detectable signals is indicative of the abundance of the first binding agent in the reaction mixture. In preferred embodiments, such targets are differentially labeled, e.g., with different fluorescent dyes. For example, the targets can be labeled with different types of FRET acceptors, and the binding agents can be labeled with the same type of FRET donor, such that emission of signal from a first FRET acceptor on a first target indicates a first binding agent is bound to the first target. Optionally, a detectable label on a first target can be removed upon binding of a first binding agent, and loss of signal from the detectable label is indicative of binding of the first binding agent to the first target.

In further aspects, methods for labeling a target molecule with a fluorescent label are provided herein. In some embodiments, such methods include providing a phosphate donor comprising the fluorescent label on a phosphate to be transferred to a phosphate acceptor; providing a kinase enzyme that can accommodate the phosphate donor; introducing the target molecule to the kinase enzyme bound to the phosphate donor; and providing reaction conditions to favor transfer of the fluorescent label from the phosphate donor to the target molecule by the kinase enzyme, thereby labeling the target molecule with the fluorescent label. In certain preferred embodiments, the phosphate donor is a phospholinked nucleotide and/or the kinase enzyme is aminoglycoside phosphotransferase. The target molecule is typically immobilized in an optical confinement, e.g., a zero mode waveguide.

In yet further aspects, methods for sequencing a DNA component of chromatin are provided herein. In certain embodiments, such methods include lysing a cell comprising the chromatin; priming the DNA component of the chromatin to produce a primed region of the DNA component; binding a polymerase to the primed region to generate a polymerase-chromatin complex; immobilizing the polymerase-chromatin complex at a reaction site, thereby providing an immobilized complex; exposing the immobilized complex to a reaction mixture comprising differentially labeled nucleotides suitable for template-directed nascent strand synthesis; monitoring the immobilized complex during template-directed nascent strand synthesis catalyzed by the polymerase, wherein the monitoring comprises detecting an order of the differentially labeled nucleotides incorporated into a nascent strand complementary to the DNA component; and determining a sequence of the portion of the DNA component complementary to the nascent strand, thereby sequencing the DNA component. Priming of the DNA component can be accomplished in various ways, e.g., by providing a primer complementary to the primed region or nicking the DNA component. Optionally, the monitoring can include detection of characteristics of the template-directed nascent strand synthesis in addition to the order of the differentially labeled nucleotides incorporated into the nascent strand, such as characteristics that are indicative of (i) a feature of the chromatin related to regulation of replication or transcription; (ii) a location of a histone protein bound to the DNA component; (iii) a modification of a histone protein bound to the DNA component; (iv) a modification within the DNA component; or (v) a modification within the nascent strand. The chromatin can optionally be isolated by immunoprecipitation after lysis and prior to priming the DNA component.

In certain aspects, methods of detecting histone-DNA interactions are provided herein. In certain embodiments, such methods include providing a histone-DNA complex comprising a FRET donor linked to a histone bound to a DNA molecule; providing a FRET acceptor linked to the DNA molecule; immobilizing the histone-DNA complex at a reaction site that is optically resolvable from other reaction sites; monitoring the reaction site to detect signal from the FRET pair that is indicative of proximity between the FRET donor and FRET acceptor, thereby detecting histone-DNA interactions. In alternative embodiments, the FRET acceptor is linked to the histone bound to the DNA molecule, and the FRET donor is linked to the DNA molecule. The method can further include priming the DNA molecule and contacting the DNA molecule with a polymerase in the presence of nucleotides to detect histone-DNA interactions during template-directed nascent strand synthesis. In some cases, the histone comprises a modification, e.g., one or more methylations, acetylations, phosphorylations, ubiquitinations, sumoylations, citrullinations, or ADP-ribosylations. Such modifications are optionally linked to a detectable label that does not interfere with the FRET pair and is optically distinct therefrom.

In some aspects, methods for detecting chromatin-mediated regulation of polymerase reactions are provided herein. In certain embodiments, such methods include providing an immobilized chromatin complex comprising a DNA template and subjecting the DNA template to a polymerase reaction. One or more characteristics of the polymerase reaction are monitored as the polymerase traverses the DNA template. The DNA template is subsequently removed from the chromatin complex to produce a naked DNA template, which is subjected to a polymerase reaction. One or more characteristics of the polymerase reaction are monitored as the polymerase traverses the naked DNA template. The characteristics of the polymerase reaction on chromatin and on naked DNA are analyzed to identify regions of the DNA template at which chromatin-mediated regulation of polymerase reactions is occurring. For example, regions of the DNA template at which the characteristics monitored during the polymerase reactions differ depending on whether chromatin or naked DNA are used as a template are identified as regions at which chromatin-mediated regulation of polymerase reactions can occur. In some embodiments, the chromatin comprises a histone having a modification, e.g., one or more methylations, acetylations, phosphorylations, ubiquitinations, sumoylations, citrullinations, and ADP-ribosylations. In certain embodiments, the DNA template has at least one methylated nucleotide.

In further aspects, methods are provided for determining the accessibility of a genomic region in a given cell to an RNA therapeutic. In certain embodiments, a cell is lysed and a chromatin-bound DNA comprising the genomic regions is immobilized at a reaction site. The chromatin-bound DNA is subjected to template-directed nascent strand synthesis, and the reaction is monitored to identify the sequence of a nascent strand synthesized to identify a portion complementary to the genomic region. One or more characteristics of the template-directed nascent strand synthesis of the complementary portion are analyzed and used to determine the accessibility of the genomic region.

In yet further aspects, methods for detecting binding between a first binding partner and a second binding partner are provided herein. For example, such methods can include immobilization of a first binding partner in an amphipathic aggregate, which is positioned at a reaction site, either before or after the immobilization. Typically, only a single amphipathic aggregate is resident at a single reaction site, i.e., the reaction site does not comprise multiple amphipathic aggregates. The first binding partner is exposed to a reaction mixture comprising a second binding partner; and a signaling event indicative of binding is detected, thereby detecting binding between the first binding partner and the second binding partner. The signaling event preferably comprises an emission from a detectable label linked to at least one of the first binding partner and the second binding partner, and can optionally comprise an emission indicative of a proximity between a first detectable label linked to the first binding partner and a second detectable label linked to the second binding partner and/or an altered emission of a detectable label linked to the amphipathic aggregate. In some cases, the signaling event is dependent upon uptake of the second binding partner into an aggregate-confined reaction volume. The amphipathic aggregate can be a micelle, liposome, or lipid bilayer confining a reaction volume, and can further be directly or indirectly immobilized at the reaction site.

In addition, methods are provided for generating a random array of optically resolvable polymer molecules of known monomer composition. Such methods can comprise providing an array of optically resolvable reaction sites, and synthesizing a single polymer molecule at each of the optically resolvable reaction sites, wherein the synthesizing comprises exposing the reaction sites to a reaction mixture comprising a pool of differentially labeled monomers under conditions that promote incorporation of the differentially labeled monomers into the single polymer molecule. Each of the reaction sites is monitored during the incorporation of the differentially labeled monomers to generate a set of time sequences of incorporations of the differentially labeled monomers at each of the reaction sites, thereby generating a random array of optically resolvable polymer molecules of known monomer composition. In certain preferred embodiments, the synthesizing further includes providing a protecting group on each of the differentially labeled monomers, wherein the protecting group prevents incorporation of multiple differentially labeled monomers at a single reaction site; incorporating a single differentially labeled monomer comprising the protecting group at the single reaction site; detecting the single differentially labeled monomer incorporated; removing the protecting group from the single differentially labeled monomer detected; and repeating the steps until the single polymer has been synthesized. The differentially labeled monomers preferably comprise detectable labels, such as fluorescent dyes, with each type of monomer having a optically distinct detectable label so that it can be both identified and distinguished from other types of monomers. In some cases, the detectable label is linked to the protecting group of a monomer. The polymer can be essentially any polymer, e.g., a polysaccharide, polypeptide, polynucleotide, etc. The optically resolvable reaction sites are preferably within optical confinements, e.g., zero mode waveguides.

Further methods are provided for simultaneously or sequentially generating both interaction characteristic(s) and reactant characteristic(s) for a single reaction complex. In some embodiments, such methods comprise providing a reaction site on a substrate and immobilizing a single molecule or molecular complex at the reaction site to produce an immobilized reaction component. A reaction mixture comprising a plurality of types of non-immobilized reaction components (at least some of which are preferably binding partners for the immobilized reaction component) is introduced to the immobilized reaction component at the reaction site, and an interaction between the immobilized reaction component and the non-immobilized reaction components is monitored. Two or more characteristics of the interaction are identified and analyzed to identify (i) a particular type of non-immobilized reaction component in the interaction ("reactant characteristic(s)"), and (ii) an aspect of the interaction between the immobilized reaction component and the non-immobilized reaction component interacting therewith ("interaction characteristic(s)"). The reaction site is preferably within an optical confinement, e.g., a zero mode waveguide. The immobilized reaction component is optionally a single protein molecule, a single nucleic acid, a single molecular complex comprising at least one protein molecule and at least one nucleic acid molecule, a single molecular complex comprising multiple nucleic acid molecules, and a single molecular complex comprising multiple protein molecules. In certain embodiments, the immobilized reaction component is synthesizing and comprising a nascent polymer, and further wherein at least some of the non-immobilized reaction components are binding partners for the nascent polymer. In preferred embodiments, the non-immobilized reaction components are differentially labeled (e.g., with fluorescent dyes) to permit optical distinction during the reaction. The interaction characteristic(s) can include affinity, on/off rates, association and dissociation constants, and the like.

Yet further methods are provided for simultaneously or sequentially generating both interaction characteristic(s) and reactant characteristic(s) for a set of different types of single reaction complexes. In some embodiments, such methods comprise providing an array of reaction sites on a substrate and immobilizing a plurality of types of single molecules or molecular complexes at the reaction sites to provide a plurality of types of immobilized reactants at a plurality of reaction sites. In preferred embodiments, each or a majority of reaction sites comprises only a single immobilized reaction component. A reaction mixture that comprises a non-immobilized reaction component is introduced to the reaction sites, and an interaction between one of the immobilized reaction components and the non-immobilized reaction component is monitored to identify two or more characteristics of the interaction.

The characteristics are analyzed to identify (i) a particular type of immobilized reaction component immobilized at the reaction site at which the interaction took place ("reactant characteristic(s)"), and (ii) an aspect of the interaction between the immobilized reaction component and the non-immobilized reaction component interacting therewith ("interaction characteristic(s)"). In certain preferred embodiments, the reaction site is within an optical confinement, e.g., a zero mode waveguide. The non-immobilized reaction component is optionally an antibody, ligand, substrate, nucleic acid, cofactor, toxin, hormone, transcription factor, nucleic acid binding agent, or protein binding agent. In certain embodiments, the plurality of types of immobilized reaction components are complexes synthesizing and comprising a nascent polymer, wherein each different type comprises a different nucleic acid encoding the nascent polymer such that each type of immobilized reaction component comprises a different nascent polymer. In some embodiments, the monitoring includes detecting a fluorescent label attached to said one of the immobilized reaction components, where a change in emission from the fluorescent label is indicative of binding to the non-immobilized reaction component. The interaction characteristic(s) can include affinity, on/off rates, association and dissociation constants, and the like.

DETAILED DESCRIPTION OF THE INVENTION

I. General

Figure 1:
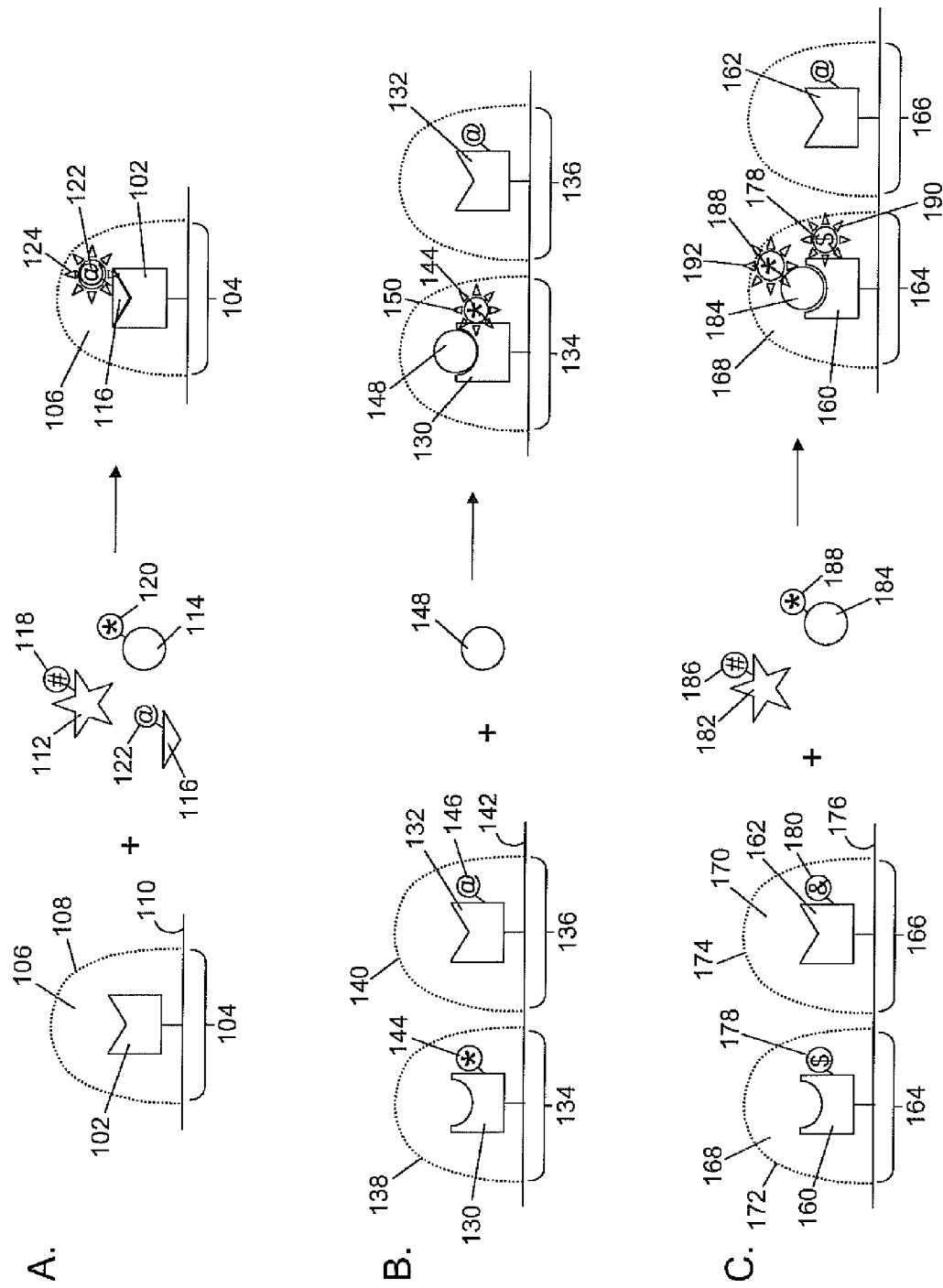
FIGS. 1A, 1B, and 1C provide illustrative examples of various methods of detecting interactions between immobilized and non-immobilized reaction components.

The present invention is generally directed to compositions, methods, and systems for performing single-molecule, real-time analysis of a variety of different biological reactions. The ability to analyze such reactions provides an opportunity to study those reactions as well as to potentially identify factors and/or approaches for impacting such reactions, e.g., to stimulate, enhance, or inhibit such reactions.

Certain methods of the invention exploit the optical isolation properties of optical confinement techniques, such as zero mode waveguide technology, total internal reflection fluorescence (TIRF) microscopy, optical waveguide technology, and the like. In particular, the invention provides for observation of the interaction of two or more specifically interacting reactants at the single molecule (or single molecular complex) level in order to monitor the progress of the interaction separately from other interactions. In other words, a single immobilized reaction component can be monitored at a single reaction site on a support such that signals received from that reaction site are optically resolvable from other immobilized reaction components at other reaction sites on that support. In preferred embodiments, the methods monitor optically detectable labels inside an optical confinement, such that a single reactant comprising an optically detectable label in an optical confinement is distinguishable from a different single reactant comprising a different optically detectable label in a different optical confinement. A plurality of analytical reactions may also be carried out in an array of optical confinements. Analytical reactions in an array of optical confinements can be carried out simultaneously, and may or may not be synchronized with one another. Preferably, in such an array, a reaction taking place in a first optical confinement is optically resolvable from a reaction taking place in a second optical confinement, and they two reactions can therefore be monitored simultaneously and independently.

The monitoring typically comprises providing the interaction with one or more signaling events that are indicative of one or more characteristics of that interaction. Such signaling events may comprise the retention of a labeled reactant within a given observation region, or the interaction of two or more interactive labeling components to produce a signal characteristic of the interaction, e.g., based upon proximity of two interacting label components. For example, in some embodiments, the labels emit optical signals that are detected by an optical detection system operably linked to a reaction site at which the analytical reaction is taking place. As used herein, a reaction site is a location on or adjacent to a substrate at which an analytical reaction is monitored, and may refer to, e.g., a position on the substrate at which one or more components of an analytical reaction are immobilized or to an effective observation volume (or "detection volume") within which an analytical reaction is monitored. The detected signals are analyzed to determine one or more characteristics of the analytical reaction, e.g., initiation, termination, affinity, biochemical event (e.g., binding, bond cleavage, conformational change, etc.), substrate utilization, product formation, kinetics of the reaction (e.g., rate, time between subsequent biochemical events, time between the beginning/end of subsequent biochemical events, processivity, error profile, etc.), and the like. These characteristics may generally be broken into two categories: reactant characteristic(s) and interaction characteristic(s). Reactant characteristic(s) includes characteristics of a particular reactant, e.g., type/identity of reactant, concentration of the reactant, a label on the reactant, etc. Interaction characteristic(s) includes characteristics of a given interaction between multiple reactants, e.g., rates, constants, affinities, etc., and is typically determined based on reaction data gathered during such an interaction. For example, some characteristics of a polymerization reaction include the identity of a monomer incorporated into a growing polymer, the rate of incorporation, length of time the polymerase is associated with the template, and the length of the polymer synthesized. In some embodiments, various different components of an analytical reaction (e.g., different types of monomers) are differentially labeled to allow each labeled component to be distinguished from other labeled components during the course of the reaction. For example, incorporation of monomer A into a polymer can be distinguished from incorporation of monomer B.

In certain preferred embodiments, multiple characteristics of a reaction are monitored and/or determined. For example, these may be multiple characteristics of one or more reaction components (e.g., identity, concentration, etc.; "reactant characteristic(s)"), one or more characteristics of an interaction between two or more reaction components (e.g., related to product formation, kinetics of the reaction, binding or dissociation constants, etc.; "interaction characteristic(s)"), or, preferably, a combination reactant characteristic(s) and interaction characteristic(s). In some embodiments, a reaction mixture comprises a plurality of types of non-immobilized binding partners, and a characteristic determined is the particular type of one of the non-immobilized binding partners, e.g., that associates with a particular reaction site. In some embodiments, an array of reaction sites comprises a plurality of types of immobilized binding partners, each at a different reaction site, and a characteristic is determined that identifies which type of immobilized binding partner is located at each of the different reaction sites. In some embodiments, an array of reaction sites comprising a plurality of types of immobilized binding partners, each at a different reaction site, is contacted with a reaction mixture comprising a plurality of types of non-immobilized binding partners; characteristics determined during the reaction serve to both identify which of the types of immobilized binding partners is located at each reaction site and which of the types of non-immobilized binding partners associate with the immobilized binding partners. In some cases, a non-immobilized binding partner comprises a first detectable label and an immobilized binding partner comprises a second detectable label, where co-localization of the first and second detectable label is indicative of an interaction between the non-immobilized and immobilized binding partners, e.g., where features of the colocalization (e.g., residence time, on/off rate, etc.) are consistent with such an interaction. In other cases, the specificity of the interaction between the non-immobilized and immobilized binding partners is high enough that detection of a label on a non-immobilized binding partner residing at a particular reaction site is sufficient to identify the immobilized binding partner at that reaction site. In some embodiments, a characteristic is determined that quantifies a particular aspect of an interaction between reaction components, e.g., affinity between an immobilized binding partner and a non-immobilized binding partner, a rate of catalysis of a reaction, or other aspects of the interaction. Typically, different signaling events (e.g., different detectable labels on one or more reaction components) are used to monitor or determine different characteristics of a reaction under observation, but in some embodiments a single signaling event can provide more than one type of characteristic information. For example, if a non-immobilized binding partner can have a detectable label that not only identifies it from a plurality of different non-immobilized binding partners, but also that provides kinetic information about the reaction based on various parameters monitored in real time, e.g., the time it takes for binding to occur, the time it remains associated with the reaction site, the on/off rate, etc. While certain embodiments utilize detection strategies comprising detectable labels, it will be understood that other detection strategies are also applicable to the methods herein, including those described in the literature and/or elsewhere herein, e.g., in the section entitled "Detection Strategies."

In some embodiments, multiple different interactions or reactions can occur and be monitored simultaneously or sequentially, where each individual interaction is monitored separately from every other, e.g. in an optical confinement, such that there is optical resolvability between different interactions under observation. For example, multiple different non-immobilized reaction components may simultaneously or sequentially interact with an immobilized reaction component; e.g., the multiple different non-immobilized reaction components can be different non-immobilized binding partners for an immobilized binding partner, or different agents that may alter an interaction between two reaction components, or different monomers for incorporation into a polymer being synthesized at the reaction site. In other embodiments, an interaction between a non-immobilized reaction component and a product of a synthesis reaction occurs during the synthesis reaction, e.g., once the product is suitable for such interaction. For example, the product may need to be of a certain length, or in a certain conformation (e.g., in a particular higher-order structure) to be suitable for interaction with the non-immobilized reaction component. Alternatively, a synthesis reaction can be performed at a reaction site, and subsequently exposed to a reaction mixture comprising non-immobilized reaction components that can then interact with the product of the synthesis reaction, which is preferably immobilized at the reaction site. In preferred embodiments, the synthesis reaction is monitored to determine characteristics of the product (e.g., length, chemical composition, etc.) being synthesized. Knowledge of characteristics of the product of synthesis combined with the detection of an interaction with a particular reaction component provides additional characteristics, e.g., the binding site for the particular reaction component. For example, if a polypeptide is being synthesized and the sequence of amino acid incorporations monitored in real time, then a rate of synthesis and the passage of the nascent polypeptide out of the ribosome can be monitored. Since a non-immobilized reaction component can only bind a region of the nascent polypeptide after it has been synthesized, and typically after it has exited the ribosome, the timing of such interaction is indicative of the region of the polypeptide to which the non-immobilized reaction component binds. In yet further embodiments, binding of a non-immobilized reaction component to a product of a synthesis reaction provides a characteristic of the product other than its sequence. For example, where the non-immobilized reaction component requires a particular conformation of the product, binding is indicative that the conformation has been achieved. Some protein variants fail to form the correct higher-order (e.g., secondary or tertiary) structure, and binding of a non-immobilized binding partner that is specific for the correct higher-order structure is indicative that the nascent polypeptide has the correct structure. In certain aspects, an array of immobilized nascent polypeptides is synthesized and screened in this manner to identify a) the sequences of the polypeptides at each reaction site, and b) those that bind the non-immobilized binding partner, and therefore have the correct higher-order structure.

In yet further embodiments, two reactions (reaction A and reaction B) can be performed, where reaction A identifies an immobilized reaction component at a reaction site, and reaction B characterizes an interaction of one or more non-immobilized reaction components with the immobilized reaction component. For example, reaction A can be a synthesis reaction that is monitored to identify a sequence of monomers in a nascent polymer. Alternatively, reaction A can be a specific interaction between the immobilized reaction component and a tagged non-immobilized reaction component that serves to simply identify the immobilized reaction component. For example, antibodies specific for different immobilized reaction components can be applied to an array of reaction sites to "map" the locations of the different immobilized reaction components on the array. Yet further, the immobilized reaction components can be tagged with a label that is identifiable via a reaction rather than emission of a detectable signal. For example, immobilized reaction components can be tagged with oligonucleotides, where each different type of immobilized reaction component is tagged with an oligonucleotide of a particular sequence. The oligonucleotide tags are subjected to template-directed sequencing using differentially labeled nucleotides, and the sequencing reaction is monitored in real time to determine the sequence of each tag at each reaction site, and therefore the type of immobilized reaction component at each reaction site. Typically, reaction B is an interaction between the immobilized reaction component, now identified, and a non-immobilized reaction component. Reaction B is monitored in real time to provide various characteristics of reaction B, e.g., rates, affinities, association and dissociation constants, and others described herein. In some embodiments, reaction A precedes reaction B, in other embodiments, reaction B precedes reaction A, and in yet further embodiment reactions A and B can be performed partially or completely simultaneously.

In certain aspects, a detectable label on a non-immobilized reaction component is detected upon interaction (e.g., binding), and where multiple different non-immobilized reaction components are present, they can be differentially labeled to allow differentiation during the course of the reaction. Alternatively, or in addition, a conformational change can cause a detectable change, e.g., due to an increase or decrease in intrinsic fluorescence, or to a change in the orientation of interactive labels (e.g., FRET labels) on the non-immobilized reaction component, the immobilized reaction component, or both. Such a conformational change that occurs upon interaction (e.g., binding) can be used to further distinguish between a non-immobilized reaction component diffusing near the immobilized reaction component and a non-immobilized reaction component actually binding to the immobilized reaction component.

In some embodiments, one or more reactions can be iteratively performed at a reaction site. For example, in some embodiments a reaction is performed using various different reaction conditions but the same interacting reaction components to determine the effects of reaction conditions on the reaction. In other embodiments an immobilized reaction component is subjected to multiple different reactions, e.g., by sequential exposure to different interacting reaction components. Alternatively or additionally, an immobilized reaction component can be subjected to multiple different reactions in the presence of different agents to be screened for their effect on the reaction under observation. As noted elsewhere herein, an immobilized reaction component (e.g., binding partner) is preferably immobilized such that a signal emitted from or proximal to the immobilized reaction component is resolvable from other signals emitted from or proximal to other immobilized reaction components. This orientation facilitates the observation of a single molecule or molecular complex and reactions or interactions involving the same.

In particular examples, an optically confined reaction site (also referred to as an "optical confinement" herein), such as a reaction site within a zero mode waveguide, proximal to an optical waveguide, or illuminated by TIRF, is used to provide for observation of individual molecules. In particular, one member of an interacting reactant pair, e.g., an enzyme, receptor, cell surface protein, ligand, antibody, antigen, binding agent, substrate, nucleic acid template, lectin, carbohydrate, etc., or combinations or complexes thereof, is provided immobilized within an observation volume of a zero mode waveguide or waveguide array. In certain embodiments, the reaction component that interacts with the immobilized component is provided with a labeling group such that when that interactive reactant comes into contact with the immobilized reactant, the label becomes detectable (e.g., by entering the observation volume) and/or produces a detectable signal that is characteristic of the interaction.

In some cases, the characteristic signal may derive from a single label on a non-immobilized reaction component that produces a signal duration indicative of a specific interaction, e.g., as a result of binding and/or reaction with the immobilized component. For example, one may immobilize a receptor protein within the observation volume, and interrogate that receptor with a fluorescently labeled ligand. Binding of the ligand to the receptor yields an increased retention time of the fluorescent label within the observation volume. Such a signal may also or additionally be derived from a native biomolecule, e.g., the intrinsic fluorescence of a protein containing tryptophan, tyrosine, and/or phenylalanine. Alternatively or additionally, interactive label components may be provided on different reaction components in the analytical reaction. For example, one label component can be provided on the immobilized reactant, while the other label group is provided on the non-immobilized component, or both are provided on either immobilized or non-immobilized reaction components. The different label components are selected such that whey they are placed in sufficiently close proximity, such as during the interactive reaction between the two reactants, they produce a characteristic signal for that proximity, and consequently, that reaction. Alternatively or additionally, interactive label components may be provided on a single immobilized or non-immobilized reaction component that undergoes an alteration that changes the orientation of the label components (e.g., alters the distance between them) in such a way as to change the signal emitted from the labeled reaction component during its participation in the reaction. For example, Förster resonant energy transfer (FRET) pairs may be employed that yield a characteristic fluorescent signal when the two components or two portions of a single component are sufficiently close to each other, such as when a substrate is bound in the active site of an enzyme, when a receptor binds to its ligand, or when a reaction component undergoes a conformational change, including but not limited to release of a portion of the reaction component. Similarly, quenchers may also be employed to cause a characteristic loss in fluorescent signal when the quencher and a label are sufficiently close to each other, or a characteristic increase in fluorescent signal when the quencher and label are moved away from each other.

The present invention is applicable to various different biological analyses and can be used to monitor single molecules (or molecular complexes) in such analyses in real time. Certain nonlimiting examples of such reactions include phosphorylation and dephosphorylation; receptor-ligand binding; complex formation; drug screening assays; hybridization assays; etc., specific examples of which are described herein. Biological reactions comprising a molecular complex that can be immobilized in an optical confinement and one or more reaction components that can be detectably labeled and monitored in real time are particularly appropriate for monitoring and analysis in accordance with the teachings herein. Biological reactions in which a distinct detectable signal is emitted in association with a specific biochemical reaction event (e.g., phosphorylation, binding/complex formation, dissociation, etc.) are particularly suitable.

The methods and systems provided herein can be used for testing the effects of various agents on a biological reaction, e.g., in vitro. Such agents may be drug candidates and the methods would constitute a pharmaceutical screening method for a given model system. For example, the ongoing biological reactions could be monitored in real time at a single-molecule (or single-molecular complex) level for various kinds of effects on the characteristics of the reactions, including but not limited to rate, processivity, fidelity, error profile, ligand preference, binding duration, and various other aspects (e.g., other kinetic characteristics) specific for a particular biological reaction of interest. Further, these assays can be incorporated into diagnostic kits for preparing and/or carrying out such reactions, e.g., in a home, laboratory, or clinical setting.

II. Binding Assays

In certain aspects, methods, compositions, and systems for detection of binding events are provided. One or more different reaction components may be immobilized at a reaction site, and one or more different reaction components may be labeled (e.g., differentially labeled), depending on the particular biological reaction to be monitored. In certain embodiments, at least one reaction component is immobilized and at least one non-immobilized reaction component is labeled, where during the course of the reaction the labeled reaction component is recruited to the reaction site and the constituent label detected, e.g. by binding of the labeled reaction component to the immobilized reaction component. One advantage to the methods herein is that the single molecule/molecular complex/reaction context allows a single interaction between reaction components to be monitored, measured, and/or manipulated, and the data collected can then be attributed to the single molecule/molecular complex/reaction under observation. This is not possible with bulk detection methods commonly described in the literature in which a collection of molecules, complexes, or reactions are observed as a unit rather than as individuals. The data typically corresponds to averages or means for the collection, and are not attributable to a single molecular interaction or reaction.

As used herein, "binding partners" refers to a plurality of reaction components that interact with each other, whether transiently or over an extended period. Such binding partners include but are not limited to proteins, nucleic acids, carbohydrates, phage particles, antibodies/antigens, small molecules, toxins, pathogens (e.g., bacteria, viruses, etc.), ligands, substrates, enzymes, cofactors, receptors, binding agents, lectins, metabolites, hormones, pheromones, organelles, etc., and combinations and complexes thereof (e.g., ribosome, proteosome, polymerase complex, etc.). For example, many biological molecules have highly specific interactions with one another, and some examples include, but are not limited to, lectins and their sugar moieties, antibodies and antigens, receptors and ligands, and transcription factors and their binding sites. Binding partners may be obtained (e.g., extracted or purified) from a biological sample, e.g. a cell lysate, bodily fluids or excrement, tissue or cells of a particular developmental or cell cycle stage, tissue or cells of a particular disease or non-disease state, a sample comprising one or more unknown microorganisms, an environmental sample (e.g., contaminated with some biological entity), and the like. In some embodiments, an immobilized binding partner is labeled, but does not emit a detectable signal unless complexed with a non-immobilized binding partner, e.g., due to a conformational change or proximity of the label on the immobilized binding partner and a second label on the non-immobilized binding partner. Further, various agents (e.g., activators, coactivators, toxins, drugs, drug candidates, small molecules, antibodies, inhibitors, etc.) can be tested for their effect on such an interaction.

Such binding assays are particularly useful in drug development applications and the massively parallel screening they provide can increase the efficiency of identifying new product leads by rapidly and precisely identifying a specific interaction between binding partners of interest. Through the technology of combinatorial chemistry, libraries of small molecules can be produced and screened for bioactivities. (See, e.g., *Combinatorial Chemistry and Molecular Diversity in Drug Discovery* (1998), E. M. Gordon (Editor), ISBN: 978-0-471-15518-8, which is incorporated herein by reference in its entirety for all purposes.) However, identification of those few molecules worth moving into the highly laborious and expensive drug development pipeline still requires use of complex, error-prone, and low throughput wet-lab assays. In certain aspects, the present invention provides a platform to support rapid, accurate, and high throughput screening of these large libraries of small molecules. For example, a drug target of interest can be immobilized at a plurality of reaction sites on an array and the array exposed to a plurality of small molecules from such a library, where preferably each reaction site comprises no more than one molecule of the drug target of interest. In this way, multiple small molecules can be screened on a single array and their binding to single immobilized drug targets can be monitored in real time. In certain embodiments, a binding event is detected as a signal or change in signal during the assay. For example, the drug target may undergo a change in emission upon binding, which may increase or decrease emission, or may change some other aspect of the signal (e.g., wavelength, etc.). Where the small molecules are detectably labeled, a detected signal can be a retention of a label at the location of the immobilized drug target. The assay can be performed under various conditions, e.g., differing concentrations of small molecules, pH, ion concentrations, salt concentrations, temperature, and the like. Statistical analysis of the binding of a given small molecule to an immobilized drug candidate provides various characteristics of the binding, such as affinity, rates of association and dissociation, duration of binding, etc.

In other embodiments, a plurality of different drug targets is immobilized, each at a different reaction site on an array. A single type of small molecule is introduced to the array under conditions that promote binding to one or more of the immobilized drug targets. Binding of the single type of small molecule to one or more of the different drug targets is detected, e.g., by virtue of the presence of detectable labels, interactive labels, signals related to conformational changes, or combinations thereof. In some cases, the identity of a drug target at a given reaction site can be determined by a detectable label carried by the drug target, and this detectable label can optionally have a different emission signal depending on whether it is in a bound or unbound state. For example, the unbound emission signal may be relatively low compared to a higher intensity signal produced upon binding, or vice versa. In other examples, interactive labels may be used, e.g., such that a signal identifying the drug target is emitted prior to binding, and upon binding the signal changes due to FRET with a second label on the drug target. Alternatively, interactive labels may be used, e.g., such that a label on the drug target is only excited upon binding with a small molecule that carries a detectable label having an emission spectrum that excites the label on the drug target. Thus, a signal identifying the drug target is emitted only upon binding of a small molecule. In yet further embodiments, a plurality of different drug targets is immobilized, each at a different reaction site on an array, and a plurality of types of small molecules are introduced to the array under conditions that promote binding between immobilized drug targets and small molecules. Binding of a single type of small molecule to one of the different drug targets is detected, e.g., by virtue of the presence of detectable labels, interactive labels, signals related to conformational changes, or combinations thereof. For example, a first set of detectable labels can be used to differentially label each different drug target, and a second set of detectable labels can be used to differentially label each type of small molecule. A colocalization of a label from the first set and a label from the second set is indicative of an interaction between a specific drug target and a specific small molecule. Other labeling and detection strategies may also be utilized, as further described elsewhere herein.

Deconvolution of the data to determine which compound is most "active" (e.g., bound tightest, fastest, or caused a desired conformational change in the drug target) can be achieved through the use of combinatorial pooling and mixing approaches as used in many standard high-throughput approaches. One such method has been described for deconvolution of complex genomic data (Erlich, et al. (2009) Genome Research 19:1243-53, incorporated herein by reference in its entirety for all purposes). Their approach permits simultaneous analysis of tens of thousands of specimens, and relies on the use of combinatorial pooling strategies in which pools rather than individual samples are assigned identifiers (e.g. run codes or "barcodes"). Thus, the identity of a particular specimen is encoded within the pooling pattern rather than by its association with a particular sequence tag. Decoding the pattern allows the sequence of an original specimen to be inferred with high confidence, and more than 100,000 different samples can be analyzed using only a few hundred barcodes. Although the authors describe the method in terms of identification of the source of sequence reads, this method can also be applied to deconvoluting any series of pooled samples organized in a fixed grid pattern (such as a high throughput sample plate, e.g., 1536 well, ZMW array, etc.). For example, in the case of chemical screening on arrays, a particular mixture of compounds is assigned a run code, and this mixture is screened on an array. A plurality of such mixtures, each comprising a different subset of the library to be screened and a different run code, are generated and tested on identical arrays. The results from the multiple screenings of different combinations of compounds are statistically analyzed (e.g., using a decoder program and other algorithms) to determine which contain the one or few compounds of interest, and based on knowledge of the composition of each mixture, the particular compounds that are most active are identified.

In some embodiments, a single type of binding partner (BP1) is bound or otherwise immobilized at a plurality of reaction sites on a substrate, where the reactions sites can be within ZMWs or other nanoholes, or at other types of optically resolvable reaction sites or optical confinements on an array. Excess BP1 that does not bind is preferably removed, e.g., by washing, buffer exchange, chelation or scavenging of the unbound BP1, etc. A second binding partner carrying a detectable label, BP2, is introduced to the array under conditions that promote binding to BP1. Binding of BP2 to BP1 is monitored to directly measure the characteristics of the binding. For example, BP2 can be first introduced at a low concentration, binding measured, and the concentration subsequently increased, and binding measured at the increased concentration of BP2. The increase can be gradual, e.g., as a titration, or can be "stepped" such that an additional bolus of BP2 is introduced to jump the concentration at a desired time during the analysis. In certain embodiments, three or more different concentrations of BP2 are tested. Data can be analyzed to determine the relationship between the concentration of BP2 and the number of binding event, and to determine other binding characteristics, such as $K_a$, $K_d$, $k_{on}$, $k_{off}$, $IC_{50}$, etc. In certain embodiments, different non-immobilized binding partners can be tested using the same array, e.g., to determine their relative binding kinetics (e.g., affinity, etc.) for binding to BP1, e.g., using saturation kinetics. Further, competitive assays may be performed by simultaneously exposing immobilized BP1 to multiple different non-immobilized binding partners (e.g., BP2, BP3, BP4, etc.) and monitoring binding of the multiple different non-immobilized binding partners to determine various characteristics of their interactions in a competitive environment, e.g., relative binding affinities, on/off rates, etc.

In other embodiments, an array comprising different immobilized binding partners, e.g., at known locations, can be interrogated with one or more binding partners simultaneously or sequentially to detect interactions in real time. Similarly, an array comprising different immobilized binding partners, e.g., at unknown locations, can be interrogated with one or more binding partners simultaneously or sequentially to detect interactions in real time. For example, the different immobilized binding partners can be differentially labeled such that a signal emitted from the label identifies a particular binding partner. These label can be detected prior to or during a binding assay, e.g., to map out the locations of each different kind of immobilized binding partner on the array. Such an array can be exposed to a single type of non-immobilized binding partner, which is thereby screened for interaction with one or more of the immobilized binding partners. Alternatively, the array can be exposed to a mixture of multiple types of non-immobilized binding partners (e.g., differentially labeled), which are thereby screened for interaction with one or more of the immobilized binding partners. As noted elsewhere herein, various different labeling strategies can be used in the single molecule real time assays provided, both those described herein and otherwise known in the art.

FIG. 1 provides illustrative examples of certain embodiments of methods for detection of binding between immobilized and non-immobilized reaction components. FIG. 1A shows a single immobilized reaction component 102 at a reaction site 104 having an observation volume 106 shown as the area under the dotted line 108 but above the surface 110. Non-immobilized reaction components 112-116 are differentially labeled with detectable labels 118-122, respectively. The non-immobilized reaction components are introduced to the reaction site 104 and therefore the immobilized reaction component 102. Upon binding of one of the non-immobilized reaction components 116 to the immobilized reaction component 102, detectable label 122 is brought into observation volume 106, where it emits a detectable signal 124 that is indicative that immobilized reaction component 102 bound to non-immobilized reaction component 116 rather than either of non-immobilized reaction component 112 or non-immobilized reaction component 114.

FIG. 1B provides another illustrative example showing a plurality of different types of immobilized reaction components 130 and 132 immobilized at reaction sites 134 and 136, respectively. The observation volumes of reaction sites 134 and 136 are the areas beneath dotted lines 138 and 140, respectively, but above the surface 142. Immobilized reaction components 130 and 132 are differentially labeled with detectable labels 144 and 146, respectively. Non-immobilized reaction component 148 is introduced to the reaction sites 134 and 136, and therefore to the immobilized reaction components 130 and 132. Upon binding of non-immobilized reaction component 148 to immobilized reaction component 130, detectable label 144 emits a detectable signal 150 that is indicative that non-immobilized reaction component 148 bound to immobilized reaction component 130 rather than immobilized reaction component 132. The detectable signal 150 may be a result of a conformational change in immobilized reaction component 130 that occurs upon binding to non-immobilized reaction component 148, e.g., that makes label 144 available for excitation and emission. Similarly, a label on the immobilized reaction component can emit a signal prior to binding, and this signal is altered (e.g., terminated, enhanced, reduced, etc.) by the binding of a non-immobilized reaction component. Such embodiments allow mapping of the immobilized reaction components on the surface prior to exposure to the non-immobilized reaction components.

FIG. 1C provides a further illustrative example showing a plurality of different types of immobilized reaction components 160 and 162 immobilized at reaction sites 164 and 166, respectively. The observation volumes 168 and 170 of reaction sites 164 and 166 are the areas beneath dotted lines 172 and 174, respectively, but above the surface 176. Immobilized reaction components 160 and 162 are differentially labeled with detectable labels 178 and 180, respectively. Not-immobilized reaction components 182 and 184 are differentially labeled with detectable labels 186 and 188, respectively. The non-immobilized reaction components are introduced to the reaction sites 164 and 166 and therefore to the immobilized reaction components 160 and 162. Upon binding of one of the non-immobilized reaction components 184 to the immobilized reaction component 160, detectable label 188 is brought into observation volume 168. The presence of label 188 within observation volume 168 results in emissions 190 and 192 from labels 178 and 188, respectively, that are indicative that immobilized reaction component 160 bound to non-immobilized reaction component 184. Emissions 190 and 192 may both be optically detectable, e.g., resulting in an emission spectrum with two or more peaks. Alternatively, labels 178 and 188 may be interactive labels. For example, label 178 may be a FRET acceptor and labels 186 and 188 may be different FRET donors such that the signal emitted by label 178 in the presence of label 188 is optically distinct from the signal emitted by label 178 in the presence of label 186. The presence of label 188 within observation volume 168 causes an emission that excites label 178, which then emits a detectable signal indicative that non-immobilized reaction component 184 (rather than non-immobilized reaction component 182) bound to immobilized reaction component 60 rather than to immobilized reaction component 162.

In certain specific embodiments, a receptor (e.g., cell surface receptor) is immobilized and exposed to a reaction mixture comprising a set of differentially labeled candidate ligands. Detection of one of the candidate ligands being retained at the reaction site (e.g., by virtue of detection of the label attached thereto) is indicative of a binding event between the receptor and the ligand. Further analysis of these binding events can be used to assess different characteristics of a) the interaction between the binding partners (e.g., binding affinity, rate of association and/or dissociation, etc.) and/or b) one or more of the binding partners (e.g., identity, abundance, etc.) using standard biochemical and statistical calculations. Further, such characteristics can be tested in real time under various reaction conditions (e.g., different concentrations of ligand, different buffer components or concentrations thereof, different temperatures, etc.).

In other specific embodiments, a promoter region comprising an activator binding site from a gene of interest can be immobilized and various differentially labeled transcriptional activators can be tested to determine which of them can associate with the activator binding site. Further, a labeled RNA polymerase can be included to indicate if the binding of a particular activator to the activator binding site is sufficient to recruit the RNA polymerase to the promoter. In other embodiments, a transcript can be immobilized and used to screen a mixture of cellular RNAs for those that can hybridize to the transcript, e.g., to identify those involved in RNAi or other forms of RNA-based transcriptional regulation. In some embodiments, a signal may only be emitted if both the activator and the RNA polymerase associate with the promoter, e.g., using a FRET pair or other interactive labeling strategy. An advantage to these real time methods is that the reaction conditions can be changed during the course of the reaction (e.g., by buffer exchange, adding agents or drugs, changing the temperature, etc.) to allow multiple different reaction conditions or different sets of non-immobilized binding partners to be tested during the course of a single analytical reaction, which is not possible with end point reactions for which a single measure is produced at the end of the reaction.

In yet further embodiments, a set of nucleic acid templates comprising known sequences is bound to a different reaction site in an array. A reaction mixture comprising nucleic acid binding agents whose identity and/or abundance is unknown is introduced to the array, and binding of the nucleic acid binding agents to the nucleic acid templates on the array is monitored, e.g., by optical means. In certain preferred embodiments, the nucleic acid binding agents are differentially labeled, and the association of one of them with a nucleic acid template results in a detectable signal that can be monitored, recorded, and further analyzed. For example, the emission spectrum of the detectable signal identifies the nucleic acid binding agent bound to the template. The amount of binding to a particular nucleic acid template is correlated with the abundance of a nucleic acid binding agent specific for that nucleic acid template in the reaction mixture. The array is preferably an array of optical confinements, e.g., a ZMW array. The nucleic acid binding agents may include, e.g., transcription factors, polymerases, reverse transcriptases, helicases, histones, nucleases, methyl binding proteins, restriction enzymes and other nucleases, phosphatases, groove binders, intercalators, antibodies, and other nucleic acid binding proteins. Although described in terms of an array of nucleic acid templates, other immobilized binding partners may also be subjected to such a multiplex analysis of binding agents present in a reaction mixture.

In related embodiments, a set of nucleic acid templates comprising unknown sequences is bound to a different reaction site in an array. For example, the set of nucleic acid templates may comprise a set of degenerate Oligonucleotides. A reaction mixture comprising known nucleic acid binding agents is introduced to the array, and binding of the nucleic acid binding agents to the nucleic acid templates on the array is monitored, e.g., by optical means. In certain preferred embodiments, the nucleic acid binding agents are differentially labeled, and the association of one of them with a nucleic acid template results in a detectable signal that can be monitored, recorded, and further analyzed. For example, the emission spectrum of the detectable signal identifies the nucleic acid binding agent bound to the template. Optionally, the nucleic acid templates are subjected to single molecule sequencing either prior to or following the binding assay, to determine the sequence of the template at each reaction site. Alternatively, the nucleic acid templates may be subjected to hybridization with labeled oligonucleotides, with the strength of hybridization corresponding to the complementarity of a given template to a given labeled oligonucleotide. The array is preferably an array of optical confinements, e.g., a ZMW array. As above, the nucleic acid binding agents may include, e.g., transcription factors, polymerases, reverse transcriptases, helicases, histones, nucleases, methyl binding proteins, restriction enzymes and other nucleases, phosphatases, groove binders, intercalators, antibodies, and other nucleic acid binding proteins. The sequences of the set of nucleic acids that interacts with a given nucleic acid binding agent can be further analyzed to determine a consensus binding sequence for the nucleic acid binding agent.

Figure 2:
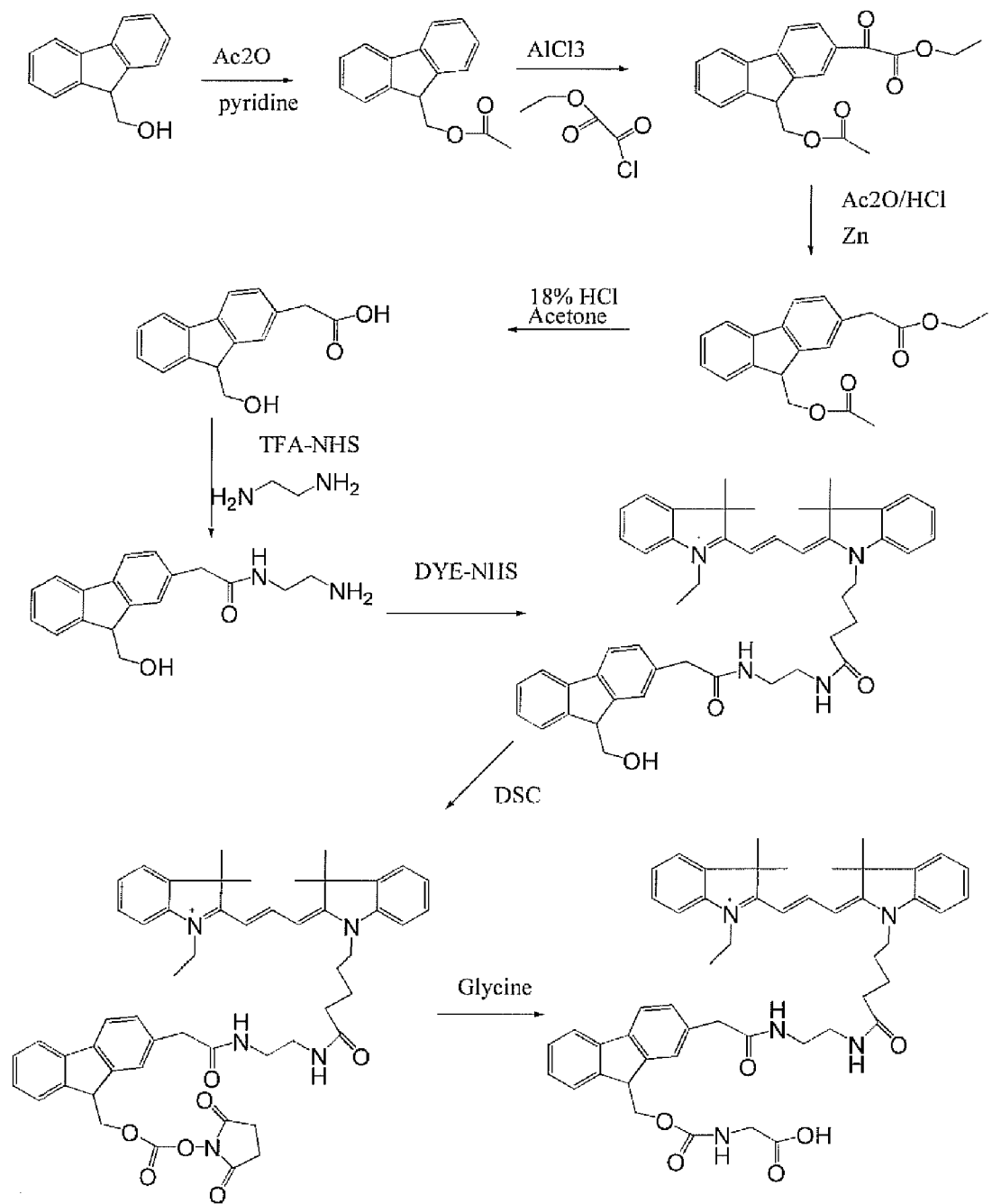
FIG. 2 provides an exemplary scheme for synthesis of dye-labeled Fmoc amino acid monomers showing initial, intermediate, and final chemical structures in panels A-I.
Figure 3:
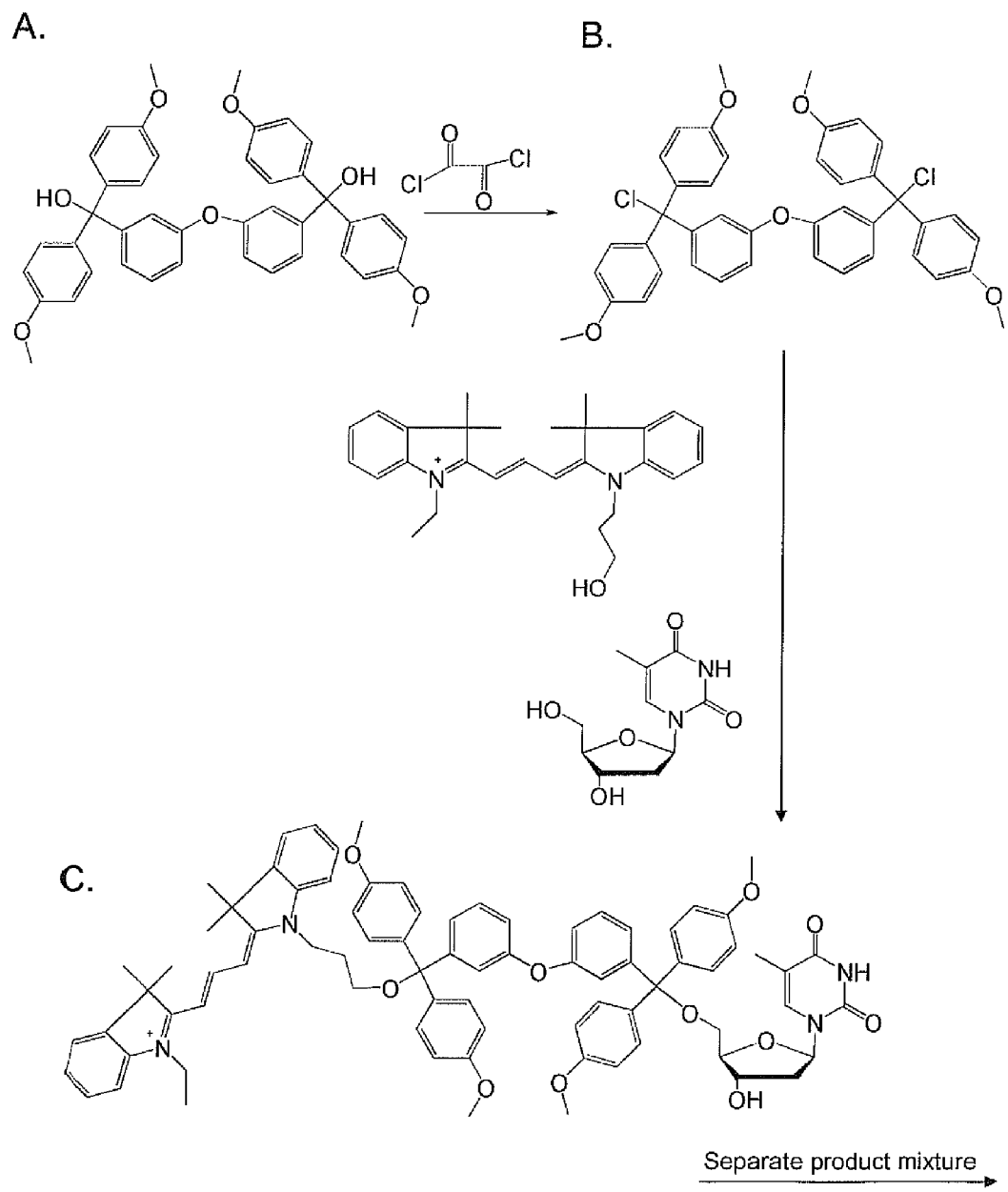
FIGS. 3A, 3B, 3C and 3D provide an exemplary scheme for synthesis of dye-labeled DMTr nucleoside phosphoramidite monomers.

In certain embodiments, set of polymers to be analyzed is synthesized, each polymer in the set being synthesized at a different reaction site in an array of reaction sites. The sequences of the polymers may be controlled by introducing, in a pre-determined order, a plurality of monomers to the reaction site. Preferably, each of the incorporated monomers has a protecting group to prevent the addition of multiple monomers to the template during each round of incorporation, and a detectable label that is indicative of the type of monomer so incorporated. The protecting group and the detectable label can be linked together, so that removal of the protecting group also removes the detectable label, or vice versa. For example, certain intermediates developed for other applications are known in the art, e.g., in Liu, et al. (1990) Int J Pept Protein Res. 35(2):95-8; and Oka, et al. (2004) Bioorg Med Chem. Lett. 14(12):3241-4, the disclosures of which are incorporated herein by reference in their entireties for all purposes. Certain exemplary schemes for the synthesis of dye-labeled monomers appropriate for these methods and applicable in conventional solid phase synthesis protocols are provided in FIGS. 2 and 3. FIG. 2 provides a synthesis scheme for dye-labeled Fmoc (fluorenylmethyloxycarbonyl) amino acid monomer synthesis; and FIG. 3 provides a synthesis scheme for dye-labeled DMTr (dimethoxytrityl) nucleoside phosphoramidite monomer synthesis. As will be clear to those of ordinary skill in the art upon review of the teachings herein that other detectable labels, protecting groups, or derivitization schemes known in the art can also be used to generate the arrays of individual polymers. In certain embodiments, such polymers are polypeptides and the monomers are differentially labeled amino acids. In other embodiments, the polymers are polynucleotides and the monomers are differentially labeled nucleotides.

Figure 4:
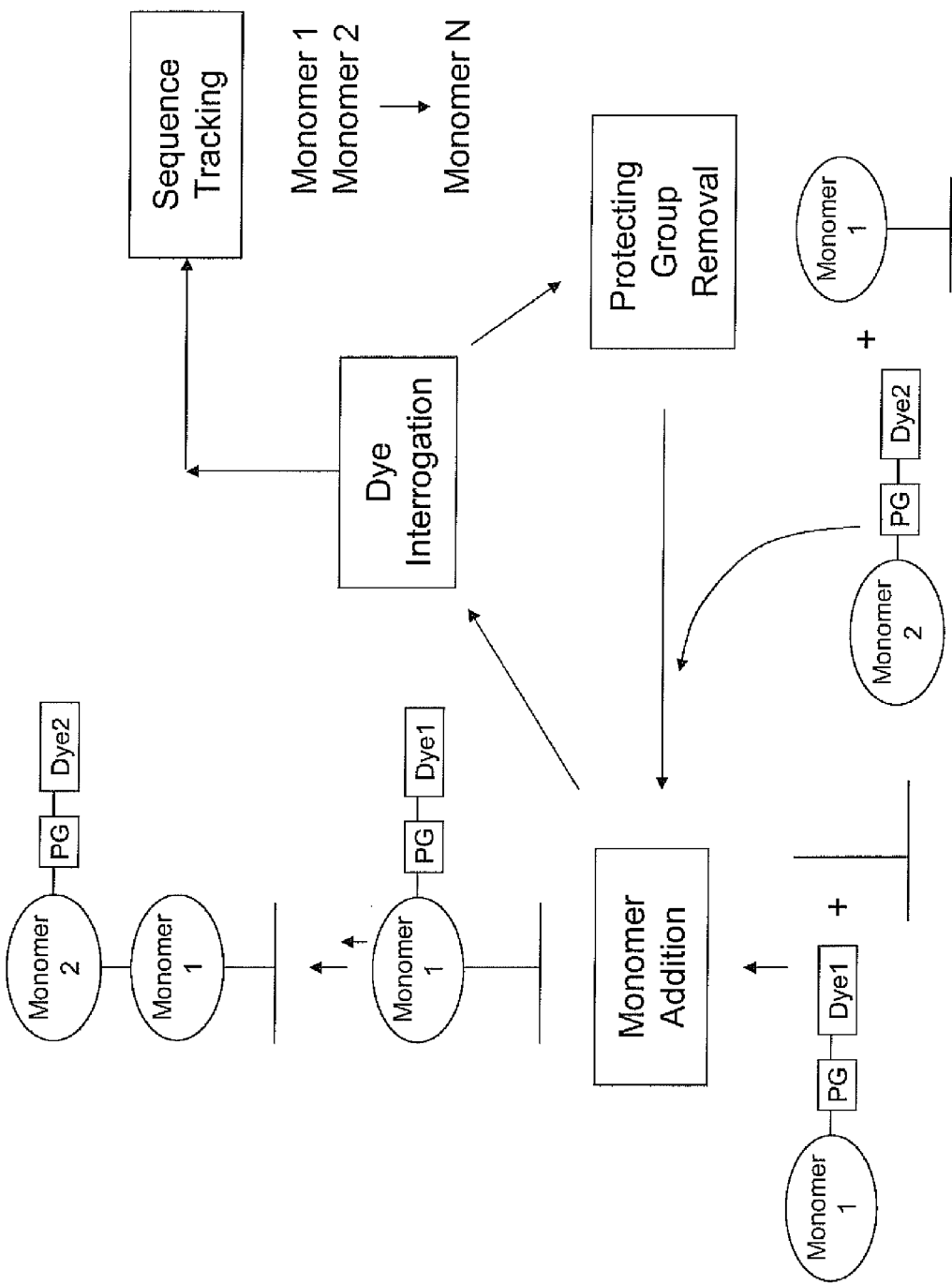
FIG. 4 illustrates an exemplary synthesis scheme for randomly synthesizing polymers.

Further, the methods can be used to generate a "random array" comprising single, randomly generated polymers at known reaction sites. The sequence of each polymer is determined during synthesis and its location on the array mapped. The synthesized and mapped randomly generated polymers can be subjected to various analyses with full knowledge of their monomer composition. Standard solid phase synthesis methods are used with detectably labeled protecting groups at the growing end of the monomer chain. Using a mixture of monomers, each type of monomer in the mixture having a unique self-identifying label, allows the identity of the added monomer at each cycle to be to be tracked. The detectable label with the protecting group is removed at the beginning of the next synthesis cycle. Although the actual synthesis is random since any monomer in the mixture can be incorporated in each cycle, the sequence synthesized at each reaction site is tracked by detecting the monomer incorporated at each cycle. A general scheme for an exemplary solid phase synthesis method is shown in FIG. 4.

In aspects of the invention, an analytical reaction is monitored to detect binding to a newly synthesized molecule or a molecule or molecular complex comprising a newly synthesized portion. Preferably, such newly synthesized molecules comprise biological molecules, such as polypeptides, carbohydrates, and nucleic acids (e.g., DNA, RNA, DNA-RNA hybrids, etc.). Alternatively, newly synthesized molecules may be small molecules, such as drugs or drug candidates, or may be synthetic polymers. Binding is monitored in real time by virtue of detectable labels linked to binding agents that may interact with the newly synthesized molecules. In preferred embodiments, immobilized reaction complexes are multiplexed on a substrate such that each newly synthesized molecule or molecular complex is detectably resolvable from other newly synthesized molecules or molecular complexes associated with the substrate, thereby allowing single-molecule resolution of not only the binding assays, but also the synthesis reactions.

In some embodiments, a reaction in which an enzyme is synthesizing a polymer is monitored to detect binding of an agent (other than the enzyme) to the polymer produced. For example, a reaction in which a polymerase enzyme is processing a nucleic acid template can be monitored to detect binding of an agent to a polynucleotide produced during the reaction. In certain embodiments, the reaction comprises real-time, single-stranded template-directed nascent strand synthesis by the polymerase enzyme, which is monitored to detect binding of a nucleic acid binding agent to the nascent strand being synthesized or to a duplex comprising the nascent strand and the template processed by the polymerase. Preferably, the oligonucleotide used to prime the single-stranded template does not contain a sequence corresponding to a binding site for the binding agent. Nucleic acid binding agents include, but are not limited to, complementary nucleic acids, transcription factors, histone and other proteins, restriction enzymes and other enzymes, antibodies, DNA-damage binding proteins, etc. Further, use of a known set of nucleic acid templates can be used to generate an array of known polynucleotide products; and by using a random or unknown (e.g., degenerate) set of nucleic acid templates, and array of unknown polynucleotide products can be generated.

In other examples, a reaction in which a ribosome is processing a nucleic acid template can be monitored to detect binding of an agent to a polypeptide produced during the reaction. In certain embodiments, the reaction comprises real-time, single-stranded template-directed nascent polypeptide synthesis by the polymerase enzyme, which is monitored to detect binding of a polypeptide binding agent to the nascent polypeptide being synthesized. For further details of such polypeptide synthesis reaction, see U.S. Ser. No 11/399,292, filed Jun. 11, 2010 and incorporated herein by reference in its entirety for all purposes. Preferably, the agent that binds the newly synthesized polymer comprises a detectable label that emits a signal when bound. Detection of the detectable label being retained at the reaction site is indicative that the product has been bound by the agent. In certain embodiments, multiple different binding agents are present in the reaction mixture, and each is distinctly labeled to allow identification of the agent once bound to the product. Polypeptide binding agents include, but are not limited to, other proteins, enzymes, antibodies, chaperone proteins, nucleic acids, small molecules, toxins, cofactors, etc. Further, use of a known set of nucleic acid templates can be used to generate an array of known polypeptide products; and by using a random or unknown (e.g., degenerate) set of nucleic acid templates, and array of unknown polypeptide products can be generated.

Various solution conditions (e.g., pH, temperature, ion concentrations, addition of agents, such as drugs or antibodies, etc.) can be tested for their effect on binding activity. Further, variants (e.g., comprising mutations, substitutions, missing domains, fusions, etc.) of the non-immobilized or immobilized binding partners can be tested for binding activity. For example, in some embodiments a plurality of nucleic acid templates are screened to determine which contain a binding site for a particular nucleic acid-binding agent of interest, and the sequences of the nucleic acid templates that are bound can be subjected to statistical analysis to determine a consensus binding sequence for the agent. In other embodiments, a cell lysate is applied to nucleic acid templates having known sequences that include one or more binding sites for known nucleic acid-binding agents, and monitoring polymerase reactions comprising those nucleic acid templates to determine the identity and abundance of particular nucleic acid-binding agents in the lysate based upon which and how many reactions sites show retention of detectable labels corresponding to the particular agents. It will be understood that the methods are applicable to various different kinds of nucleic acid templates, nascent strands, and double-stranded products, including single-stranded DNA; double-stranded DNA; single-stranded RNA; double-stranded RNA; DNA-RNA hybrids; nucleic acids comprising modified, missing, unnatural, synthetic, and/or rare nucleosides; and derivatives, mimetics, and/or combinations thereof.

In some aspects of the invention, a reaction in which an enzyme is processing a reaction component is monitored to detect a modification (e.g., oxidative damage, abasic sites, methylation, demethylation, mutation, acetylation, deacetylation, cross-linking, phosphorylation, dephosphorylation, ubiquitination, sumoylation, citrullination, and ADP-ribosylation, etc.) within a product of the reaction. Such a modification may be present in the starting reaction component, introduced by the enzyme during the reaction, or may be due to the presence of an agent in or condition of the reaction mixture (e.g., reactive oxygen species, damaging radiation, etc.) In some embodiments, an agent that specifically binds the modification ("modification-binding agent") is included in the reaction mixture. The product is preferably a nucleic acid product of template-directed nucleic acid synthesis, e.g., double-stranded or single-stranded DNA, RNA, or DNA-RNA hybrid, and the modification may be present in the template strand or nascent strand. In certain preferred embodiments, a nucleic acid template is a circular molecule. In certain aspects, a reaction in which an enzyme is processing a template further comprises an agent that allows bypass of a modification that blocks processing of the template by the enzyme, thereby allowing read-through and continued processing of the template downstream of the modification. For example, where a circular template is being processed by a polymerase capable of strand-displacement, the agent can allow displacement of a nascent strand comprising a modification where the polymerase in the absence of the agent is unable to or inefficient at displacing the modification-containing strand from the circular template. Monitoring reactions in which an enzyme is processing a template to produce a product that comprises a modification generates data that can be statistically analyzed to determine the number and locations of the modification in the product, and can potentially identify the type of modification, as well.

In certain preferred embodiments, the nascent strand is synthesized using differentially labeled nucleotides and monitored in real time such that the sequence of the nascent strand is determined based upon the series of labeled nucleotides incorporated by the polymerase. This sequence read information can be used to derive the binding site for the binding agent that subsequently binds to the nascent strand or duplex comprising the nascent strand. In certain preferred embodiments, the template-directed synthesis and binding reactions are performed such that a single reaction (e.g., comprising only one template molecule, one polymerase enzyme, and one nascent strand) can be monitored separately from other reactions, e.g., by virtue of optical resolvability of the reaction site. For example, a single polymerase/template complex can be immobilized at a single, optically resolvable reaction site, e.g., in a nanohole, zero mode waveguide, etc. Single molecule resolution allows determination of characteristics of a binding reaction at the single molecule level (e.g., to measure binding affinity, on/off rates, association/dissociation constants, etc.). For example, the binding affinity of the binding agent to the binding site can be estimated by measuring the length of time the binding agent remains associated with the single- or double-stranded product of the synthesis reaction ("residence time") based on the length of the emission signal that corresponds to the label on the binding agent.

In certain embodiments, the binding agent is a transcription factor comprising a detectable label, binding of the transcription factor to the newly generated duplex comprising the nascent strand is indicative that the duplex includes a binding site specific for the transcription factor, and this binding is detected by the presence of an emission signal corresponding to the transcription factor. The sequence read information generated during the template-directed synthesis reaction is used to derive the nucleotide sequence of the region to which the transcription factor binds. Further, the binding affinity of the transcription factor to the binding site can be estimated by measuring the residence time of the transcription factor on the double-stranded product of the synthesis reaction, as described above.

In other embodiments, the binding agent is specific for hemimethylated sequences, e.g., a maintenance methyltransferase. Binding of a maintenance methyltransferase to a newly synthesized duplex is indicative that the template comprised a methylated base, and such assays can be used to map methylated site in nucleic acid samples, e.g., genomic samples. The binding agent could also be a doubly-methylated binding protein (e.g. the MBD, or methyl-binding domain, family of proteins). In alternative embodiments, the binding agent is an RNAi agent (e.g., miRNA, siRNA, etc.) and the newly synthesized strand is mRNA. Binding of the RNAi agent indicates that the mRNA contains a target binding site for the agent, and the sequence of the mRNA is used to derive the sequence of the target binding site. Identification of the agent (e.g., based upon a detectable label thereon) and the target binding site can provide insight into regulation of gene expression. In yet further embodiments, the binding agent is a nucleic acid damage recognition agent (e.g., enzymes involved in base excision repair, nucleotide excision repair, mismatch repair, and cell cycle checkpoints), and its binding to the newly synthesized duplex is indicative that either the template or the newly synthesized strand comprises damage, e.g., abasic site, oxidative damage, etc. Other types of binding agents are know in the art and can be used in the methods described herein. For example, see U.S. Ser. No. 12/635,618, filed Dec. 10, 2009, the disclosure of which is incorporated herein by reference in its entirety for all purposes.

In some embodiments, a plurality of different single-stranded templates are used, where different templates have different nucleotide sequences. Synthesis of the nascent strand produces a double-stranded product whose sequence can be determined based on the sequence of nucleotides incorporated, and the reactions are further monitored to determine which double-stranded sequences comprise binding agent binding sites. Alternatively or additionally, multiple differentially labeled binding agents can be screened on an array comprising multiple copies of the same single-stranded template and/or different single-stranded templates. The different single-stranded templates can be from any source, including but not limited to fragmented and denatured whole genomic DNA, genomic DNA enriched for regions of interest, e.g., promoter regions, amplified DNA, and randomly generated oligonucleotides. In certain embodiments, synthetic templates comprise multiple different candidate transcription factor binding sequences, e.g., separated by gap regions known not to comprise transcription factor binding sequences. Preferably, the gap sequences are long enough that the time it takes the polymerase to traverse a gap is long enough to allow binding of a transcription factor to the previously synthesized candidate region prior to synthesis of the subsequently synthesized candidate region. In certain embodiments, synthetic templates are prepared and subsequently amplified using a mutagenic polymerase to increase the diversity of the synthetic template library. In yet further embodiments, synthetic templates can be from a library constructed from de Bruijn sequences of size k. A de Bruijn sequence of size k is a sequence of minimal length that contains all sequences of length k. (See, e.g., Berger, et al. (2006) Nature Biotechnology 24:1429-1435, the disclosure of which is incorporated herein by reference in its entirety for all purposes.) Where multiple different single-stranded templates are found to be bound by the same binding agent, a consensus sequence can be determined based upon the similarities between the different sequences bound, e.g., by comparing the sequences of the newly synthesized strands for the different single-stranded templates and/or their corresponding nascent strands.

III. Chromatin Sequencing and Histone Decoding

In certain aspects, methods are provided for studying histone structure and function. In cells, DNA is not naked, but is wrapped around histones and interacts with other proteins to form chromatin. Histones are the main protein component of chromatin, and DNA winds around them like thread around a spool. In this way, DNA and histones are also to be considered binding partners in the context of the disclosure herein. This interaction serves many functions, such as compacting the DNA and controlling gene expression. The interaction of DNA with histones (tightness of wrapping, periodicity of wrapping, loci at which histones are associated, etc.) is altered by modifications to the DNA (e.g., mutation, methylation, etc.) and the histones (e.g., methylation, acetylation, phosphorylation, ubiquitination, sumoylation, citrullination, ADP-ribosylation, etc.). Since the interaction between DNA and histones affects transcription and, therefore, gene expression, alteration of this interaction is an important form of epigenetic regulation. High-speed, high-throughput methods for studying DNA/histone interactions and DNA and histone modification in real time and with single molecule resolution are provided herein. Further, histones are known to associate with other nucleic acids, as well (e.g., RNA) so it is to be understood that although certain embodiments are described in terms of histones associated with DNA, the methods herein are also applicable to complexes of histones with other types of nucleic acids.

In some embodiments, single-molecule, real-time DNA sequencing is performed using chromatin rather than naked DNA. In order to maintain the native positioning of the nucleosomes on the DNA, standard DNA purification methods that remove proteins cannot be used. As such, methods that purify the chromatin from the rest of the cell lysate without disrupting the original chromatic structure are provided. In certain preferred embodiments, nuclei are isolated from cells and lysed. The nuclei can be isolated from essentially any cell type, e.g., tissue samples, cell cultures, bodily fluids or excrement, and the like. The chromatin is subjected to fragmentation, which can be accomplished by digestion with endonucleases or by shearing the chromatin in any number of ways that do not disrupt the nucleosome structure. Many different types or combinations of restriction enzymes can be used to fragment the chromatin. The average fragment size can be modulated by choosing a restriction enzyme with a specific recognition sequence. As is well known in the art, enzymes with longer recognition sequences will cut less frequently than those with shorter recognition sequences, resulting in longer fragment sizes (on average). DNA hairpins are ligated onto the ends of the chromatin fragments, and subsequent exonuclease treatment degrades any chromatin fragments that are not capped by the hairpin adapters at both ends. Depending on the termini of the fragments, the hairpins can have blunt ends or overhangs ("sticky ends"). In some embodiments, chromatin sequencing is performed using unpurified cell or nuclear lysates. In other embodiments, additional purification steps are performed to remove further isolate the chromatin from other components of the nuclear lysate. For example, chromatin is isolated by immunoprecipitation and the fixing reversed prior to subsequent analysis of the histone-bound DNA.

After lysis and chromatin extraction, the DNA is primed while still bound to the histones Priming can be performed in various ways known to those of skill in the art, e.g., by nicking with an endonuclease to create a polymerase binding site, or by fragmentation with restriction endonucleases followed by ligation of single-stranded, priming-site-containing hairpins at the termini (as described in U.S. Patent Publication Nos. 20090280538 and 20090298075, the disclosures of which are incorporated by reference in their entireties for all purposes), followed by addition of primer oligonucleotides, e.g., that bind to the single-stranded loop region of the hairpins to serve as binding and initiation sites for a polymerase enzyme. After priming, template-directed sequencing of the histone-bound DNA is performed and monitored in real time using a polymerase capable of using double-stranded DNA as a template and incorporating differentially labeled nucleotides into a nascent strand complementary to a strand of the histone-bound DNA. A polymerase that uses the histone-bound nucleic acid as a template may be a DNA polymerase or an RNA polymerase. For example, DNA replication dynamics in the presence of nucleosomes can be studied using a DNA polymerase, transcription dynamics in the presence of nucleosomes can be studied using an RNA polymerase, and reverse transcription in the presence of nucleosomes can be studies using a reverse transcriptase. In some embodiments, the activity of both a DNA polymerase and an RNA polymerase can be observed on a single nucleic acid template. For example, a single-stranded DNA template can be subjected to template-directed nascent strand synthesis in the presence of a DNA polymerase and differentially labeled dNTPs, and the product of the reaction (dsDNA) can be subjected to transcription in the presence of a DNA-dependent RNA polymerase and differentially labeled NTPs, where the labels on the dNTPs are detectably different, and so distinguishable from the labels on the NTPs. As such, both the sequence of the nascent DNA strand and the sequence of the nascent RNA strand can be determined by monitoring incorporation of the labeled dNTPs and NTPs, respectively. (Further, the nascent RNA produced can be subjected to translation in the presence of a ribosome, aa-tRNAs, and other accessory factors (e.g., EF-Tu, EF-G, GTP, etc.) to produce a nascent polypeptide, as further described in U.S. Ser. No. 11/399,292, filed Jun. 11, 2010, the disclosure of which is incorporated herein by reference in its entirety for all purposes.) Preferably, such a polymerase is immobilized at a reaction site, although in certain embodiments the template and/or one or more histone proteins can be immobilized instead of or in addition to the polymerase enzyme. Immobilization methods are provided elsewhere herein. These experiments also provide the opportunity to monitor the dynamics of a single nucleosome during replication, transcription, and reverse transcription.

In further embodiments, the reaction conditions are changed to test the effects of various factors on the synthesis reactions and/or nucleosome dynamics during synthesis. For example, various agents can be added to the reactions, such as drugs, drug candidates, small molecules, toxins, etc. Alternatively or additionally, the reaction conditions can be varied by charging pH, salt concentration, ion concentration, types of ions present, temperature, etc. In addition, the reaction components themselves can be substituted in various ways. For example, nucleosomes from different sources can be used and the results analyzed to determine how nucleosome structure varies between the different sources, e.g., different cell or strain types, tissue at different stages of development, healthy versus diseased cells or tissue, tissue or cells from different populations of individuals, tissue or cells subjected to different stressors (e.g., drug or toxin treatment), etc.

During template-directed nascent strand synthesis, detection of each nucleotide incorporation event generates a sequence read for the nascent strand, and this sequence read is used to derive a sequence of the histone-bound DNA. (Further details for methods of single-molecule, real-time, template-directed nucleic acid sequencing applicable to the methods herein are described in detail, e.g., in Eid, et al. (2009) Science 323:133-138; Korlach, et al. (2008) Nucleosides, Nucleotides and Nucleic Acids 27:1072-1083; U.S. Pat. Nos. 7,056,661; 6,787,308; 6,255,083; U.S. Ser. No. 12/635,618, filed Dec. 10, 2009; and U.S. Ser. No. 12/767,673, filed. Apr. 26, 2010, all of which are incorporated herein by reference in their entireties for all purposes.) The tightness of the interaction between the DNA template and histones will impact the ability of the polymerase to process the template and synthesize the nascent strand, so monitoring the characteristics (e.g., kinetics, etc.) of the synthesis reaction provides a way to measure both the presence of histone-DNA binding (e.g., for mapping the positions of the histones on the template) and the tightness of this interaction. For example, as the polymerase encounters a region of the DNA template that is tightly bound by a histone protein, characteristics of the synthesis reaction (e.g., rate, time between incorporation events, error profile, etc.) will change as it passes through the region, e.g., the bound region of the DNA template will be more slowly processed by the polymerase than a region of the template free of histones, thereby producing a detectable decrease in the rate of nascent strand synthesis, and possibly even cause a pause or termination of synthesis. Because the synthesis reaction is being monitored in real time, these changes in characteristics of the synthesis reaction are mapped to particular regions of the DNA and used to determine the positions of the histones bound to the DNA. For example, where a bound histone blocks continued progression of the polymerase, the sequence read generated terminates at a position proximal to the bound histone. Subsequent sequencing of the template in the absence of the histone will provide a nucleotide sequence at which the histone was bound. Alternatively, where bound histones cause only pausing but the polymerase is able to reinitiate, the pattern of pauses (e.g., upon encountering a histone or at various points while traversing a histone-bound locus) can be used to generate a map of histone "footprints" on the template.

Modifications to the DNA template (e.g., methylation, oxidative damage, other bound agents, etc.) can also be detected in this way, as further described in U.S. Ser. No. 12/635,618, filed Dec. 10, 2009, and incorporated herein by reference in its entirety for all purposes. Various characteristics of nascent strand synthesis (e.g., rate, signal intensity, error profile (e.g., incorporation of a noncognate base), processivity, time between incorporation events, residence time of a nucleotide in the binding pocket of the polymerase prior to incorporation, and the like) can be used to detect both DNA modifications and the presence of bound histones, and their "characteristic signatures" can be deconvolved by known statistical methods. For example, detection of both the methylation state of the template DNA, the regions of the template at which histones are bound, and the strength of the interaction between the template and histones bound thereto facilitates study of the interplay between these two highly important epigenetic mechanisms. Additional methods for characterizing the effect of DNA-modifying compounds on nucleosomal DNA that may be used with the teachings herein are described in Subramanian, et al. (2010) Methods Mol Biol 613:173-92, which is incorporated herein by reference in its entirety for all purposes.

In certain aspects, a histone map is generated for one or more regions of genomic DNA, or for one or more chromosomes, or for a whole genome. For example, a sample of genomic DNA within chromatin is fragmented and the resulting fragments are subjected to template-directed nascent strand synthesis at separate, optically resolvable reaction sites, e.g., ZMWs. The reaction is monitored to identify those regions of the genomic DNA that are bound to a histone, and the sequence and binding data generated across the set of reaction sites provides a map of the regions bound by histones in the genomic DNA. In certain embodiments, the histones are subsequently removed (e.g. by denaturation or protease treatment) and the resulting "naked" fragments are subjected to template-directed nascent strand synthesis to generate sequencing reads unperturbed by the presence of bound histones. This strategy is further enhanced by the use of an immobilized polymerase enzyme at the reaction site and hairpin adapters that transform linear double-stranded fragments into closed single-stranded circles (as described above). This strategy allows repeated sequencing of the template as the polymerase repeatedly passes around the template to generate redundant sequence information. The histones can be removed (e.g., by displacement by the polymerase or other treatment) after a first pass around the template, or the polymerase can repeatedly sequence the template bound by the histones prior to their removal. Likewise, redundant sequence information can be generated from the naked template by repeated sequencing by the polymerase. In some embodiments, chromatin components are present in excess with protein factors facilitating chromatin assembly during the chromatin sequencing reactions. (See, e.g., the Chromatin Assembly Kit (cat. no. 53500) from Active Motif, Carlsbad, Calif., which is incorporated herein by reference in its entirety for all purposes.) This strategy allows reformation of nucleosomes that are disassembled during processing by the polymerase enzyme, and thereby allows repeated sequencing of a single nucleosome-laden nucleic acid template.

In certain aspects, chromatin is immobilized using various capture agents (e.g., antibodies, oligonucleotides, covalent and noncovalent linkages, and others described elsewhere herein), which are bound to a reaction site and serve to immobilize a chromatin complex at the reaction site (e.g., within a zero mode waveguide). The capture agent may be specific for a particular component of the chromatin, e.g., a specific histone protein, histone modification, nucleic acid sequence, or nucleic acid modification. For example, capture agents that are specific for a particular region of the genome, such as a gene of interest, can be used to selectively immobilize chromatin comprising that region or fragments thereof. Optionally, nucleic acid fragments can be immobilized at optically resolvable reaction sites and subjected to sequencing reactions prior to exposure to labeled histones. This strategy provides a sequence map of an array, and subsequent exposure to labeled histones informs which of the immobilized nucleic acid fragments comprises a histone-binding sequence. In some embodiments, unknown (e.g., randomly generated) nucleic acid sequences are immobilized and tested to determine their ability to wind around histones, and in other embodiments nucleic acid fragments from sources of interest are isolated and immobilized. Optionally, histone proteins are immobilized at reaction sites (e.g., through methylation, acetylation or phorphorylation of the histones) and monitored for binding to non-immobilized nucleic acids in the reaction mixture, where the nucleic acids can be from any desired source, e.g., genomic fragments or randomly generated fragments. A polymerase enzyme and differentially labeled nucleotides are subsequently added, template-directed nascent strand synthesis ensues, and the sequence of the nucleic acid bound to the historic protein is determined based upon the sequence of the nascent strand generated. In yet further embodiments, multiple histones at different regions of a single DNA molecule could be immobilized at optically resolvable reaction sites. For example, histones located hundreds or thousands of bases apart on the same DNA molecule could be immobilized at different reaction sites. In some such embodiments, the interactions of the histones at the different regions of the DNA molecule monitored in real time. Alternatively or additionally, template-directed nascent strand synthesis could also be performed at the different regions of the DNA molecule, as described elsewhere herein. Thus, a single molecule of DNA could be simultaneously sequenced at multiple reaction sites, enabling linkage sequencing studies of distant genomic regions at the single molecule level.

The interaction of DNA and histones is not a static interaction but a dynamic one. For example, DNA-histone complex conformations are known to "breathe" as torsional strain within the complex relaxes. Further, assembly (e.g., binding and winding) and disassembly (e.g., unwinding and dissociation) are dynamic processes. In some embodiments, the dynamics of histone interactions with DNA are studied by linking detectable labels to one or more histone components of a nucleosome and/or to one or more regions of a template DNA molecule. Such detectable labels may simply inform as to the constitution of a complex at a reaction site, e.g., which histone proteins are present, by virtue of their presence at the reaction site. In certain embodiments, different conformations of the DNA-histone (or polymerase-DNA-histone) complex alter the emission from a detectable label, e.g., by burying it or exposing it. In some embodiments, the labels are interactive labels, such as FRET labels or quenchers, and different conformations of the DNA-histone (or polymerase-DNA-histone) complex alter the energy transfer or quenching between the labels resulting in changes in emission that are indicative of particular conformations of the complex. The complex is monitored to detect these changes in emissions, which are indicative of presence of a reaction component and/or conformational changes in the complex. These dynamics can be studies under various reaction conditions (e.g., by changing pH, temperature, salt concentration, types of monovalent and/or divalent ions present, etc.) and in the presence and absence of various agents, e.g., DNA binding proteins, small molecules, drugs, drug candidates, toxins, etc. Optionally, reaction additives (e.g., agents) could also be detectably labeled to enable detection of their interaction with the DNA-histone complex.

As noted above, histone modifications are known to affect gene expression, e.g., by impacting transcriptional regulation. A combination of histone modifications makes up the "histone code." Examples of modifications of the H3 and H4 histone tails include methylation, demethylation, acetylation, deacetylation, phosphorylation, dephosphorylation, ubiquitination, sumoylation, citrullination, and ADP-ribosylation. In addition, the cores of certain histones can be modified; these modifications are known to be important in controlling transcription and thus in regulating gene expression and have previously been shown to dramatically vary between normal and cancer tissues as well as other conditions of interest. Such modifications can be intentionally introduced by incubation with modifying enzymes, or by other chemical means known to those of ordinary skill in the art, including but not limited to exposure to ionizing radiation, oxidizing agents, reducing agents, crosslinkers, and the like. The methods herein can be used to monitor the modification of histones in real time, For example, phosphorylations of histones can be examined by detection of the addition of labeled phosphate groups, as described below. Further, other types of modifications can also be observed and measured, e.g., where a chemical moiety comprises a detectable label, the arrival or departure of which is indicative of addition or removal of the chemical moiety, respectively. In certain embodiments, the addition or removal of a chemical moiety from one or more histone proteins is detected as a change in one or more characteristics of a template-dependent nascent strand synthesis reaction, where the histone(s) is bound to the template. For example, a chromatin fragment is repeatedly subjected to the synthesis reaction, and a change in one or more characteristics of the reaction is indicative of modification of one or more histone proteins bound to the template, e.g., when those modifications change the dynamics of the histone-nucleic acid interaction in a way that eases or impedes passage of a polymerase enzyme, such as by loosening or tightening the interaction. Alternatively or in addition, histone modifications can be detected by using a labeled modifying enzyme, so that interaction with a histone is detectable by emission from the label on the modifying enzyme at the reaction site comprising the histone.

The methods herein can be used to discriminate between different types of histone modifications based on their different effects on the characteristics (e.g., kinetics) of template-directed nascent strand synthesis. Particularly preferred methods for monitoring kinetics of nascent strand synthesis are detailed in U.S. Ser. No. 12/635,618, filed Dec. 10, 2009, which is incorporated herein supra. Histone modifications may be performed in vivo, by treating cells with the necessary labeled reaction components, or may be introduced in vitro using molecular biology techniques well known and widely used in the art. Alternatively or in addition, different types of histone modifications can be differentially labeled to provide for optical detection, e.g., during template-directed nascent strand synthesis. For example, individual nucleosomes immobilized at optically resolvable reaction sites (either directly or indirectly through interaction with a molecular complex immobilized at the reaction site) can be labeled with distinct fluorophores in order to observe which of these different chemical modifications are present under various conditions. In certain embodiments, as described below, phosphorylation of histones can be performed in the presence of gamma-phosphate labeled nucleotides by transferring the label to the phosphorylated position on the histone using a kinase enzyme. Similar methods can be used to specifically label other types of histone modifications.

In certain embodiments, the interactions of histones having or lacking various modifications with each other and with nucleic acids can be tested not only to determine the effects of such modifications (or lack thereof) on the interactions, but also to determine characteristics in the nucleic acid that impact interaction with the differently modified histones. The use of interactive labels (e.g., FRET labels) can additionally inform as to the orientation of various components of a histone-DNA complex or a histone-DNA-polymerase complex, providing insight into how such modifications impact chromatin structure, and potentially replicative and/or transcriptional regulation. In some embodiments, nucleosomes from different sources (different strains, different individuals, diseased vs. healthy tissue or cells, different tissue types, different stages of development, different stages in the cell cycle, etc.) are analyzed to identify differences in histone locations, structure, modifications, and function between the sources. Further, the effects of histone locations and/or modifications (and chromatin structure changes they impart) on transcription, replication, or reverse transcription can be studied by performing template-directed nascent strand synthesis reactions (described above) on templates bound by such modified histones. For example, in certain embodiments cells are lysed at various stages of development; in other embodiments, lysates from diseased cells (e.g., cancer cells) are compared to lysates from non-diseased cells. These methods provide snapshots of histone-DNA interactions and histone modifications and relate them to cellular conditions, disease processes, drug response, and higher level environmental stresses (e.g., exposure to toxins, diet, etc.).

Data generated from template-directed nascent strand synthesis reactions performed in the presence of various types of histone modifications can be used to construct maps between histone modification patterns and regulation of these polymerase-mediated processes. Such maps are useful for identification of biomarkers that are indicative of various phenotypes (e.g., disease subtypes) and/or useful as targets for drug development. For example, targets for RNA therapeutics can be identified, e.g., by determining the accessibility of genes with respect to their chromatin structure under a given set of conditions. This information is valuable not only for selecting genes to therapeutically target, but also to better understand the conditions under which a gene-of-interest is more available, and to promote that accessibility as a part of a treatment regimen. Further, various types of drug-based screening can be performed. For example, a drug that affects histone modifications can be added to a reaction mixture and the histone-DNA complex can be monitored to determine how the changes in the histone modifications affect the dynamics of histone-DNA interactions and/or template-directed nascent strand synthesis. Further, a drug that specifically targets histones in a particular state can be added to a reaction mixture and the histone-DNA complex can be monitored to determine how the addition of the drug impacts transcription, which would simultaneously assess histone state and the transcription of regions in that state. Such single-molecule, real-time drug screening studies will provide invaluable data for understanding the effects of drug administration both with regards to the drug target and also with regards to non-target regions of the genome. Understanding of non-target effects can lead not only to identification of potential adverse events prior to a clinical trial, but can also to beneficial off-label uses for a given drug or drug candidate. Together, these strategies will greatly advance the pursuit of effective treatments for disease by providing, e.g., the ability to rapidly screen a sample for patterns of histone modifications that can be used as disease stratification biomarkers, drug engagement biomarkers, and/or drug response biomarkers, and are particularly applicable to RNA-based therapeutics screening methods. Such assays can be routinely performed in a clinical setting.

Other types of labeling strategies are contemplated, certain of which are described elsewhere herein. For example, such labeling strategies can comprise FRET labels, non-FRET labels, Q-dots, quenchers, and the like. As noted above, labeling strategies can be designed to monitor various aspects of a histone-DNA or histone-DNA-polymerase complex, including simply detecting the presence of a particular histone or DNA modification, the conformation of histone proteins and/or template wrapping, a specific interaction between the DNA template and a histone protein, or multiple characteristics of template-directed nascent strand synthesis using a chromatin template. Further, the various assays and labeling strategies can be combined in a multitude of ways to facilitate a particular assay. These studies can be performed fully in vitro, or one can apply a cell lysate to a reaction site to create a "quasi-in vivo" experimental system.

An additional benefit to direct chromatin sequencing is the more stable conformation of the nucleic acid molecule (e.g., DNA, RNA, etc.) within the chromatin structure. Large nucleic acid molecules, e.g., greater than about 5 kilobases in length, are susceptible to shearing-induced degradation during routine laboratory processes such as pipetting and stirring. (See, e.g., Lengsfeld, et al (2002) J. Pharm. Sci. 91(7): 1581-1589, the disclosure of which is incorporated herein by reference in its entirety for all purposes.) The longer the nucleic acid molecule is, the more prone it is to shearing-induced degradation. Degradation of long nucleic acid molecules prevents generation of long, single-molecule sequencing reads. In cells, millions of bases of DNA are stably wrapped around the Histones in chromatin, and the DNA in these structures does not degrade as easily as "naked" DNA. As such, sequencing nucleic acid molecules within chromatin as described above serves to stabilize it and prevent shearing-induced degradation during sample preparation.

In certain embodiments, purified nucleic acids can be combined with histones (e.g., after amplification or other types of complexity reduction techniques) prior to sequencing or other laboratory manipulations to protect the nucleic acids from shearing-induced degradation and/or to study the chromatin assembly/disassembly processes. Methods for "chromatin assembly" can be active or passive, and may occur prior to immobilization, during immobilization, or even during a synthesis reaction, e.g., replication, transcription, or reverse transcription. Some such assembly methods as well as other methods useful with the teachings herein are provided in the art, e.g., in the Chromatin Assembly Kit (cat. no. 53500) from Active Motif (Carlsbad, Calif.); Akey, et al. (2003) Curr Opin Struct Biol 13(1):6-14; Park, et al. (2005) J Biol Chem 280 (3):1817-25; Gordon, et al. (2005) J Biol Chem 280(40): 33701-6; Park, et al. (2006) Biochem Cell Biol 84(4):549-58; Chodaparambil, et al. (2007) Nat Struct Mol. Biol. 14(10: 1105-7; Watanabe, et al. (2010) Biochim Biophys Acta. 1799 (5-6):480-6; Segal, et al. (2006) Nature 442(7104):772-8; Segal, et al. (2009) Trends Genet. 25(8):335-43; Field, et al. (2008) PLoS Comput Biol. 2008 November; 4(11): and Tims, et al. (2007) Methods 41(3):296-303, the disclosures of which are incorporated herein by reference in their entireties for all purposes. By monitoring the assembly and/or disassembly of chromatin in real time, various characteristics of these processes can be interrogated and measured, including but not limited to on/off rates of chromatin assembly/disassembly, effects of various histone and/or nucleic acid modifications on assembly/disassembly, on/off rates of histone and/or nucleic acid modifying enzymes, effects of histone H1 on chromatin, and characteristics of polymerase-mediated synthesis during assembly/disassembly. For example, by labeling various protein and/or nucleic acid components of a histone-nucleic acid complex with interactive labels, changes in the emission profile are detected as these different components associate and dissociate with one another. The pattern of the changes in emission profile correlates to the changes occurring in the complex, and can be used to determine rate constants, affinities, and the like during chromatin assembly and disassembly. Different types of histones or histones with different modifications can be used depending on the desired characteristics of the resulting histone-nucleic acid complex, e.g., tighter or looser wrapping. In certain embodiments, histones can be used as anchors for immobilization of nucleic acids at a reaction site, e.g. in a ZMW. In further embodiments, a set of histones associated with different portions of a long nucleic acid can be used to immobilize the different portions of the nucleic acid at different reaction sites, thereby facilitating simultaneous analysis of the different portions of a single nucleic acid molecule. In preferred embodiments, the analysis involves real-time, template-directed synthesis of nascent strands complementary to the different portions of the single nucleic acid molecule.

IV. Methods of Analysis Using Aggregates of Amphipathic Molecules

In pharmacology, there is great interest in screening the efficacy of candidate drug binding to outer membrane portions of membrane-bound receptors (e.g., G-coupled protein receptors), the efficacy of candidate drugs at initiating signal transduction pathways inside the cell, and the efficacy of other types of drugs being trafficked from outside to inside the cell. The methods herein provide strategies for drug screening tests that are more sensitive, faster, and higher-throughput that those currently available.

In certain aspects, a single lipid micelle is confined at a reaction site to serve as a surface to which or within which a binding partner for binding assays is localized. A typical micelle is an aggregate of amphipathic molecules in an aqueous solution with the nonpolar portions in the interior and the polar portions at the exterior surface exposed to the aqueous solution. In such a micelle, the nonpolar portion comprises one or more hydrophobic "tails" and the polar portion comprises a hydrophilic "head."

Figure 5:
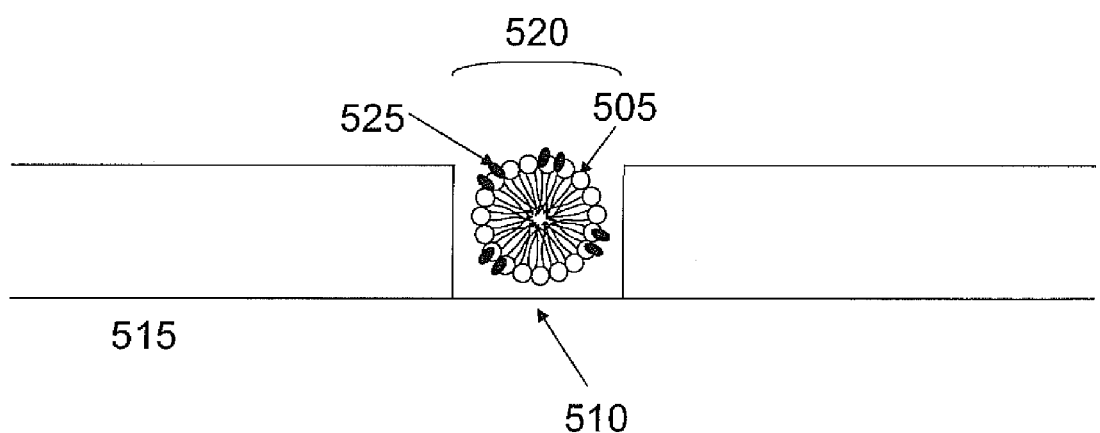
FIG. 5 provides an illustrative example of a single lipid micelle confined at a reaction site within a zero mode waveguide.

In certain preferred embodiments, as shown in FIG. 5, a single lipid micelle 505 is confined at a reaction site 510 on a surface 515 within a nanohole 520, e.g., a zero mode waveguide (ZMW). Protein receptors 525 can be seen as pairs of black ovals on the surface of the micelle 505. Deposition of a micelle in a nanohole can be achieved by various methodologies known in the art, and in certain embodiments is performed using block copolymer micelle nanolithography (see, e.g., Glass, et al. (2003) Nanotechnology 14:1153-60; and Glass, et al. (2003) Adv. Funct. Mat. 13:569-575, the disclosures of which are incorporated herein by reference in their entireties for all purposes), in which the nanoholes act as pre-structured guides for self-assembly of block copolymer micelles generated at a size to match the nanohole diameter, resulting in one micelle per nanohole. It is to be understood that ZMWs and other types of nanoholes may be used in the methods described herein, e.g., nanoholes disposed to be illuminated by an evanescent wave emanating from a channel waveguide in a solid support, e.g., as described in U.S. Patent Publication Nos. 20080128627, 20080152281, 200801552280, and 20100065726, the disclosures of which are incorporated herein by reference in their entireties for all purposes.

In certain aspects, a single liposome is confined at a reaction site to serve as a cell membrane mimic for binding assays. Like a micelle, a liposome is an aggregate of amphipathic molecules in an aqueous solution. However, the walls of a liposome are comprised of two layers of these molecules, with the outside layer having the nonpolar tails in the interior and the polar heads at the exterior surface exposed to the aqueous solution; and the inside layer having the nonpolar tails directed toward the outside layer, and the polar heads exposed to the interior, aqueous volume of the liposome. This type of wall is also referred to as a lipid bilayer. In certain preferred embodiments, a single liposome is confined at a reaction site within a nanohole, e.g., a zero mode waveguide (ZMW). Methods for confining a liposome include functionalization with one or more molecules that specifically associate with one or more molecules at a reaction site, and are described further elsewhere herein. The structure of a liposome is similar to that of a cell membrane, with aqueous environments both inside and outside the liposome. As such, molecules that traverse cell membranes can be immobilized in a liposome in their native, active conformation. For example, transmembrane proteins can be monitored for not only binding of a ligand outside of the liposome, but also for activity that occurs inside the liposome upon binding, including but not limited to transport of the ligand to the inside of the liposome. Further embodiments, are described below.

In certain aspects, a single lipid bilayer is confined at a reaction site to serve as a cell membrane mimic for binding assays. Like a liposome, a lipid bilayer is an aggregate of amphipathic molecules in an aqueous solution, where the aggregate is organized into two layers with the nonpolar tails directed toward the center and the polar heads in each layer in contact with the surrounding aqueous solution on each side of the bilayer. In certain preferred embodiments, a single lipid bilayer is confined at a reaction site within a nanohole, e.g., a zero mode waveguide (ZMW). Certain preferred aspects of preparing a reaction site comprising a lipid bilayer are described in White, et al. (2007) J. Am. Chem. Soc. 129: 11766-11775, the disclosure of which is incorporated herein by reference in its entirety for all purposes. Molecules that traverse a cell membrane can be immobilized in a lipid bilayer and monitored for binding and other activities. Further, such molecules can be oriented such that the portion that is extracellular in vivo is in the layer closest to a substrate comprising the reaction site. Alternatively, such molecules can be oriented such that the portion that is intracellular in vivo is in the layer closest to a substrate comprising the reaction site.

In certain preferred embodiments, an amphipathic aggregate has one or multiple membrane protein channels or receptors, and a reaction site is used for highly sensitive and rapid detection of binding and/or trafficking events. In some embodiments, a substrate comprises an array of reaction sites (e.g., greater than about $10^2$ to $10^6$ reaction sites, or at least about $10^4$ or $10^5$ reaction sites), and the methods also benefit from high multiplex and therefore provide increased throughput. In certain preferred embodiments, the methods benefit by using reaction sites within the optical confinement of a ZMW.

In some embodiments, binding of an aggregate-localized (AL) binding partner to a binding partner in solution (IS) is monitored. Such binding partners can be essentially any molecules that display a specific interaction, e.g., receptors and ligands (e.g., a drug or drug candidate, small molecule, hormone, etc.), antigens (e.g., cell surface displayed antigens that can be imbedded in an amphipathic aggregate) and antibodies, enzymes and substrates, nucleic acids (e.g., RNA and RNAi agents, complementary nucleic acids, nucleic acids in a higher order complex), etc. For example, binding of a ligand to a receptor is studied by immobilizing the receptor in an amphipathic aggregate in a ZMW and exposing the amphipathic aggregate to a reaction mixture comprising a ligand for the receptor (e.g., a drug, small molecule, hormone, etc.) that carries a detectable label. Optionally, multiple, differentially labeled (and therefore distinguishable) ligands can be present in the reaction mixture. When one of the ligands binds to the receptor, the detectable label is detected and the bound ligand identified by virtue of the type of label detected. In certain embodiments, the labels are fluorescent or fluorogenic labels, such as fluorescent dye molecules. Preferably, binding of a ligand having a fluorescent label brings the fluorescent label into a reaction volume having radiation (e.g., light of a given wavelength and intensity) capable of exciting the fluorescent label. When the excited fluorescent label emits the excitation energy (e.g., as light), the emission is detected and its characteristics (e.g., wavelength, intensity, etc.) used to identify the label, and therefore also the particular ligand bound to the receptor. In some embodiments, more than one molecule of a particular AL binding partner is present on a single amphipathic aggregate, and this strategy can further increase the signal indicative of binding where each AL binding partner binds to the same type of IS binding partner. For example, if there are five "X Receptors" on an amphipathic aggregate and a single, labeled "Y Ligand" binds to each, the signal will be significantly greater than if only a single Y Ligand had bound to a single X Receptor on the amphipathic aggregate. In some embodiments, only a single binding partner is resident on a single amphipathic aggregate, and this configuration is particularly beneficial where a practitioner desires to measure reaction characteristics at the single-molecule level, e.g., for analysis of weak, unstable interactions that must be analyzed over a short period of time than allowed by standard assays.

Optionally, a detectable label can be an interactive label (e.g. FRET label) whose signal emission is further modulated in the presence or absence of a second detectable label, quenching group, or the like. In certain embodiments, a first FRET label on an AL binding partner emits a first signal when it is not bound to an IS binding partner, and transfers energy to a second FRET label on the IS binding partner upon binding. The resulting emission from the second FRET label is indicative of the particular IS binding partner associated with the AL binding partner. Optionally, the first FRET label can be linked to the reaction site rather than the AL binding partner.

Other labeling strategies are also contemplated. For example, the AL binding partner can comprise a label that only emits a signal when the AL binding partner is further bound to an IS binding partner. The "dark" state of the label on the AL binding partner may be due to quenching, e.g., by a quencher attached to the AL binding partner that is only in close proximity to the detectable label when the binding pocket is vacant; or due to the sequestering of the label in the "unbound" conformation of the AL binding partner, thereby preventing its excitation in the absence of an IS binding partner. In some embodiments, binding of the IS binding partner to the AL binding partner exposes the label on the AL binding partner to excitation radiation, and subsequent emission from the label is detected and is indicative of a binding event. Optionally, the label on the AL binding partner is a FRET label and emission from the label upon binding to the IS binding partner results in excitation of a second FRET label on the IS binding partner. Emission from the second FRET label is detected and is indicative not only of a binding event, but also the identity of the IS binding partner associated with the AL binding partner. Alternatively, signal emission from the label on the AL binding partner may require energy transfer from a second label, e.g., on a binding partner in solution, to emit a signal. In some such embodiments, the energy transfer is not maximally efficient, and results in at least two different emission signals, one from the AL binding partner and one from the IS binding partner. This labeling strategy provides not only a signal indicative of the binding event, but also a signal indicative of the IS binding partner bound. Methods for labeling reaction components with FRET labels having submaximal FRET efficiencies are further described in U.S. Ser. No. 12/749,859, filed Mar. 30, 2010, the disclosure of which is incorporated herein by reference in its entirety for all purposes. Further, in some embodiments, a lipid bilayer confines an ion-sensitive fluorophore (e.g., within a liposome or in a structural confinement covered by a lipid bilayer), and the ion-sensitive fluorophore is stimulated by the flow of ions through an ion channel that forms upon binding of an IS binding partner to an AL binding partner immobilized within the lipid bilayer. A change in signal from the ion-sensitive fluorophore is indicative of a binding event that stimulates activation of the ion channel.

The methods can also be used to test various agents for the ability to change the activity or conformation of an AL binding partner, e.g., in a way that could induce a signal cascade within a cell. Emission from a label linked to the intracellular portion of the AL binding partner is monitored to detect the change in activity and/or conformation. In certain preferred embodiments, the AL binding partner is a transmembrane protein, examples of which include, G protein-coupled receptors (GPCR), transporters, ion channels, etc., and the transmembrane protein is immobilized in a lipid bilayer (e.g., in a liposome). In some embodiments, binding of a ligand specific for the Al binding partner induces a conformational change detectable by virtue of the activity of the AL binding partner, e.g., on the opposite side of the lipid bilayer. For example, binding of a ligand to a transmembrane protein can stimulate a biochemical reaction catalyzed by the transmembrane protein that alters emission, e.g., by cleavage of a substrate. In one such embodiment, a GPCR immobilized within a lipid bilayer of a liposome comprises a FRET donor on the portion of the receptor within the liposome. A GTP comprising a FRET acceptor on the terminal phosphate is bound to the portion of the receptor within the Liposome and excited by the FRET donor. Binding of a ligand to the portion of the GPCR outside the liposome causes cleavage of the terminal phosphate from the GTP, allowing the FRET acceptor to move away from the FRET donor, resulting in a consequent loss of signal from the FRET acceptor. Therefore, the loss of signal within the liposome is indicative of a binding event on the outside of the liposome. In alternative embodiments, a conformational change in the AL binding partner is induced by binding of an IS binding partner, and this conformational change alters emission from a detectable label, e.g., by sequestration or desequestration of a label bound to the AL binding partner, by changing the distance between interactive labels. For example, the intensity can be increased by movement of the detectable label away from a quencher (e.g., also bound to the AL binding partner) or by desequestration of the detectable label; the intensity can be decreased by movement of the detectable label away from a FRET donor that excites the detectable label or by sequestration of the detectable label; the wavelength of emission from the detectable label can be changed by movement away from a FRET acceptor that would otherwise absorb the emission and emit the energy at a different wavelength; and the like.

The methods can also be used to study the transport of a reaction component (e.g., drug, small molecule, hormone, etc.) across a portion of an amphipathic aggregate, e.g., through interaction with an agent associated with the amphipathic aggregate. Preferably the reaction component to be transported across the portion is detectably labeled such that a signal emission is dependent upon the transport event, e.g., is only emitted once the reaction component is enclosed within a micelle or liposome, or has passed through a lipid bilayer into a confined reaction volume, or vice versa (e.g., is transported in the opposite direction). As used herein, "aggregate-confined reaction volume" can refer to a portion of the reaction volume within a micelle or liposome, or a portion of the reaction volume localized by a lipid bilayer, e.g., within a structural confinement covered by the lipid bilater, and the methods herein are useful for monitoring the movement of a reaction component of interest either into or out of an aggregate-confined reaction volume. For example, small molecule-transporter interactions can be monitored, where the transporter can be an efflux transporter (e.g., P-glycoprotein) or influx transporter (e.g., organic cation/anion transporters). Of particular interest to the pharmaceutical industry is the study of influx and efflux transporters capable of transporting drugs into or out of cells, especially given the transport-related toxicities of certain drugs like statins and NSAIDS. The methods herein provide valuable assays for monitoring such interactions in real-time and at the single-molecule level. Further, the multiplex capabilities enable screening of massive numbers of drugs simultaneously in a single assay.

In certain embodiments, the reaction volume within which excitation can occur is completely contained on one side of a layer of an amphipathic aggregate within an aggregate-confined reaction volume. For example, the "excitation-capable" reaction volume can be contained completely within a micelle or liposome, e.g., where a micelle or liposome completely fills the ZMW or at least the portion of the ZMW comprising the evanescent field. Alternatively, the "excitation-capable" reaction volume can be contained completely beneath a lipid bilayer that covers a structural confinement, e.g., a nanowells or ZMW.

In some such embodiments, entry into a confined reaction volume is required for excitation of the label on the reaction component, so detection of a signal from the label is indicative that the reaction component has been transported through the amphipathic aggregate into an aggregate-confined reaction volume. Alternatively, a signal emitted from a reaction component can be different depending on whether the reaction component is free in solution, bound to the surface of the amphipathic aggregate, or within an aggregate-confined reaction volume. In one such embodiment, the distance from the label on the reaction component to the source of excitation emission can be suboptimal when the reaction component is bound to the outside surface of the amphipathic aggregate (i.e., outside of micelle/liposome or on surface of lipid bilayer most distal from excitation source), but can be maximized by passage of the reaction component though a portion of the amphipathic aggregate, e.g., into a micelle or liposome or through a lipid bilayer, resulting in a low intensity signal when on the surface, and a high intensity signal when internalized/transported across the bilayer. In other embodiments, a first FRET donor on the outside surface of the amphipathic aggregate causes a first change in signal upon binding, and a second FRET donor confined by the amphipathic aggregate causes a second change in signal upon passage of the reaction component through the amphipathic aggregate into the aggregate-confined reaction volume. In further embodiments, quenchers are used, either on a surface of an amphipathic aggregate or in an aggregate-confined reaction volume, e.g., to cause a detectable decrease in emission intensity. In yet further embodiments, the reaction component may be linked to a quencher that quenches emissions from other component of the reaction mixture and/or the amphipathic aggregate, e.g., from a detectable label on a surface of or in an aggregate-confined reaction volume. Alternative embodiments utilize conformational changes to regulate emission signal, e.g., where a conformational change within a reaction component upon entry into an aggregate-confined reaction volume causes a loss in emission signal, e.g., due to complex formation with a component disposed within the aggregate-confined reaction volume. These embodiments are merely exemplary, and additional labeling schemes, e.g., using combinations of those described above, will be clear to the ordinary practitioner in light of the teachings provided herein. Further, transport out of the aggregate-confined reaction volume can be detected similarly, e.g., by detection of a gain, loss, or change of one or more emission signals. For example, if a reaction component only emits a detectable signal upon entry into an aggregate-confined reaction volume, then subsequent loss of that signal can be indicative of transport out of the aggregate-confined reaction volume.

In certain aspects, amphipathic aggregate-mediated assays can be mediated by pooling amphipathic aggregates (e.g., micelles or liposomes) comprising different AL binding partners, e.g., with a single type of AL binding partner on each amphipathic aggregate. The pool of different amphipathic aggregates can be introduced to a single array of reaction sites (e.g., ZMW array) and analyzed in parallel. To identify which type of amphipathic aggregate (and therefore which AL binding partner is present) is at a given reaction site, each type of amphipathic aggregate carries a different detectable label, e.g., comprising one or more fluorescent dye molecules. For example, each type of amphipathic aggregate can have a different single detectable label, a plurality of the same different detectable label (e.g., to increase the signal), or a distinct combination of different detectable labels, as further described below. The labels can be linked to phospholipids or other molecules that embed into the surface or are taken into the interior of the amphipathic aggregate. The labels are detected after the amphipathic aggregates are placed at the reaction sites, and the type of each amphipathic aggregate at each reaction site is determined and recorded. The labels that identify the amphipathic aggregate may be retained throughout the subsequent analytical reactions, e.g., to ensure that a given amphipathic aggregate is retained at a given reaction site throughout. Alternatively, the labels may be photobleached to lower the background emissions during the subsequent analytical reactions, e.g., so their optical spectrum does not interfere with the optical spectrum of the detectable labels on the IS binding partners to be detected. Once the different amphipathic aggregates have been mapped to the array, a plurality of types of differentially labeled IS binding partners can be provided in a reaction mixture and their binding to the different AL binding partners on the amphipathic aggregates monitored and studied in a high-throughput assay format. Many different IS binding partners (e.g., small molecule drugs) can be screened simultaneously against a plurality of different AL binding partners (e.g., receptors) associated with amphipathic aggregates at the reaction sites. For example, detection of a given drug molecule at a given reaction site can be attributed to a specific interaction between the drug molecule and a receptor on the amphipathic aggregate mapped to that reaction site.

Different labeling strategies can be employed to tag each type of amphipathic aggregate is a pool of different types of amphipathic aggregates. In certain embodiments, different sets of detectable labels are used to tag the different types of amphipathic aggregates, i.e., carrying different AL binding partners. Some labeling strategies include different combinations of different labels, e.g., where no two types of amphipathic aggregates comprises the same combination of label types. Other labeling strategies include different ratios of the same types of dyes, where some different amphipathic aggregates can have peaks at the same wavelengths, but the intensities of those peaks are distinct from one another. In one such example, two labels, A and B, are used to differentially label five different types of amphipathic aggregates, where the first type of amphipathic aggregate has only label A; the second type has a ratio of 3:1 of label A to label B; a third type has a ratio of 1:1 of label A to label B; a fourth type has a ratio of 1:3 of label A to label B; and a fifth type has only label B. These labeled amphipathic aggregates all can be characterized, and therefore identified, by their distinguishable emission spectra. Yet further labeling strategies utilize include combinations of the various strategies described above, e.g., with some amphipathic aggregates having single labels, some having multiple identical labels, some having different combinations of labels, and/or some having different ratios of labels.

in certain embodiments, amphipathic aggregates are directly or indirectly bound to the reaction site. For example, a micelle or liposome that is functionalized with biotin (e.g., either through a phospholipid-linked biotin or through a biotinylated membrane protein), is incubated with streptavidin, and is subsequently bound to a biotinylated reaction site (e.g., at the bottom of a ZMW). Similarly, a micelle or liposome can include one or more streptavidin molecules that bind to biotin at a reaction site. Alternative chemical immobilization strategies are known and widely used in the art, including but not limited to use of antibodies specific for the AL binding agent (e.g., where a micelle or liposome comprises multiple AL binding agents). Alternatively, a reaction site can be functionalized with a molecule that specifically associates with functionalized phospholipids within an amphipathic aggregate. In further embodiments, magnetic particles are placed inside micelles or liposomes and a magnetic field is used to pull them onto the reaction sites. Similarly, magnetic particles can be functionalized and attached to a binding agent lodged in the lipid membrane, such as biotin.

V. Labeling with Phospholinked Nucleotides Using Kinases

In certain aspects, methods, compositions, and systems for phosphorylation and/or dephosphorylation of biological compounds (e.g., proteins and other kinase and phosphatase substrates) are provided. Further, such reactions can be detected and analyzed in accordance with the teachings herein.

Specific labeling of proteins or small molecules with fluorescent ligands is cumbersome and labor-intensive, and labeling specific targets in cells is even harder. In certain aspects, the methods provided herein facilitate this process by taking advantage of the intrinsic ability of kinases to efficiently transfer the gamma-phosphate group of a phosphate donor, e.g., ATP, to specific target molecules. A detectable label linked to a portion of the phosphate donor (e.g., gamma-phosphate) to be transferred during phosphorylation is thereby effectively and efficiently transferred to a target molecule by the kinase enzyme without the need for complicated chemical synthesis schemes. For example, when gamma-phospholinked fluorescent ATP is the phosphate donor, the kinase transfers the phosphate and the attached linker and fluorophore onto the target molecule, thereby labeling the target molecule with the fluorophore.

The methods are highly scalable and can be performed in bulk reactions or on single molecules. Various different detectable labels can be used and are described elsewhere herein, and such labels are essentially limited only by the ability of the kinase to accommodate and transfer the phospholinked label. In some embodiments, the kinase accommodates a labeling group entirely within the binding pocket, and in other embodiments a labeling group extends outside of the binding pocket but does not interfere with phosphorylation of the target molecule. For example, one oxygen of the terminal phosphate of AMPPNP is uncoordinated in aminoglycoside phosphotransferase and the terminal phosphate is visible in the space-filled protein X-ray structure provided in FIG. 3 of Burk, et al. ((2001) Biochemistry 40: 8756-8764), incorporated herein by reference in its entirety for all purposes.) In certain aspects, other phosphotransferases and pyrophosphotransferase enzymes could also be used analogously to label target molecules with detectable labels, e.g., fluorescent dyes. The substrates so phosphorylated, and therefore labeled, are useful in countless downstream applications, including but not limited to protein-protein interaction studies.

The methods for detecting phosphorylation target molecules provided herein are also applicable to analytical reactions in which phosphorylation of a single target molecule is monitored in real time. In certain preferred embodiments, multiple single-molecule, real-time analytical reactions are localized at discrete reaction sites in an array. For example, one or more reaction components (e.g., kinases, phosphatases, substrates, cofactors, etc.) are immobilized on a substrate (e.g., a zero mode waveguide) in such a way that each phosphorylation event produces a signal from a detectable label attached to one or more immobilized or non-immobilized reaction components that is optically resolvable from any other signal from any other phosphorylation event on the substrate. Such an array of analytical reactions can optionally comprise at least about 100, 1,000, 10,00, 50,000, 100,000, 500,000, or 1,000,000 individual analytical reactions, potentially creating a highly multiplex analytical capability to monitor many single analytical reactions simultaneously and in real time on a single substrate. In certain preferred embodiments, such substrates comprise one or more, preferably at least 100, 1000, 10,000, or 100,000 optical confinements, each containing a single phosphorylation reaction. A phosphorylation or dephosphorylation event is detected when there is a change in signal emission from one or more labels in the reaction site, and analysis of the signal emission change provides information about the phosphorylation or dephosphorylation event, e.g., kinetics. For example, a target molecule immobilized in a zero mode waveguide can be monitored in real time to identify a phosphorylation event by the retention of a detectable label in the zero mode waveguide.

The methods can be modified for various purposes. For example, to determine which of a set of kinases is specific for a given target molecule, the set of kinases is provided in the reaction mixture, each carrying a differently labeled phosphate donor. As such, the emission signal detected upon phosphorylation identifies not only the type of label transferred to the target, but also which of the set of kinases catalyzed the reaction. Further, by analyzing a plurality of identical target molecules one can identify a subset of the set of kinases that can phosphorylate the target. Statistical analysis can be used to characterize various characteristics of the phosphorylation reactions, e.g., by determining aproportion of target molecules phosphorylated by each of the subset of kinases, the kinetics of the reactions, and the substrate specificities of the various kinases, e.g., under different reaction conditions.

Further, the methods can be modified to identify a set of target molecules that can be phosphorylated by a single kinase. In some embodiments, the kinase is immobilized in an array format and the different target molecules are differentially labeled in the reaction mixture. Upon phosphorylation of one of the target molecules, a long pulse from the detectable label linked to that target molecule will be detected at the reaction site, and the spectral emission of the pulse will identify the particular label, and therefore the particular target molecule that was phosphorylated. In other embodiments, different target molecules are immobilized in an array format and differentially labeled with an optically distinct FRET acceptor labels. The FRET acceptor labels on the target molecules are excited by energy emitted by a FRET donor label linked to the phosphate or phosphate chain to be transferred to the target such that upon phosphorylation the FRET acceptor emits an optically distinguishable signal. As such, a single type of FRET donor is capable of exciting a set of FRET acceptors, which are distinguishable from one another by their emission spectra. Upon phosphorylation of the target molecule, the donor and acceptor FRET labels are brought into close proximity and the spectral emission from the FRET acceptor unambiguously identifies the particular target molecule(s) phosphorylated.

In further embodiments, reaction conditions can be modified in various ways, including but not limited to altering buffer conditions, pH, temperature, cofactors present, and/or addition of agents, e.g., drugs, drug candidates, toxins, and the like. Modification of reaction conditions allows further analysis of the phosphorylation (or dephosphorylation) reaction, potentially allowing not only better understanding of the basic biology of the reaction, but also providing a means to test the effects of agents on the reaction, e.g., for drug screening purposes. For example, a reaction mixture can comprise a protein kinase carrying a phosphate donor (e.g., ATP) with a detectable label linked to a phosphate to be transferred to a protein substrate, which is immobilized at a reaction site. For example, the label can be linked to the terminal phosphate of the ATP molecule. Upon entry of the protein kinase into the reaction site, a detectable signal is emitted from the label. Phosphorylation of the substrate by the kinase transfers the label to the immobilized protein substrate, thereby fixing it in the reaction site where it can emit a signal to be detected. This signal can be analyzed to determine if a phosphorylation event occurred, e.g., by confirming whether the signal is continual or transitory. If the kinase is capable of phorphorylating with multiple different phosphate donors, these donors can be differentially labeled in the reaction mixture and signals detected from labels are indicative of which donor is being used in each phosphorylation event. Alternatively, multiple kinases can be tested in the same reaction mixture by binding each type of kinase to a donor carrying a distinct label such that detection of the label in the reaction site identifies the kinase phosphorylating the immobilized substrate. Further, such an assay may be used to identify a substrate of a kinase by differentially labeling a set of candidate substrates, immobilizing them at optically resolvable reaction sites, and detecting which of the set of candidate substrates is phosphorylated by a kinase in the reaction mixture. The effects of changing conditions and/or addition of various agents on any of these reactions (e.g., rate, substrate preference, etc.) provide valuable information that may be applied to better understanding and/or modeling of the system, and could provide a means for identifying an agent useful for beneficially influencing the system in vivo.

It will be apparent to one skilled in the art that the embodiments of the invention specifically described herein are merely exemplary and that various embodiments and modifications may be made to the invention without departing from the scope and spirit of the invention. For example, although various aspects of the invention are described with reference to phosphorylation of a target molecule, it will be clear to those of ordinary skill that the methods are also applicable to analysis of dephosphorylation of a target molecule, e.g., by monitoring disappearance of a label front an optical confinement. Further, as noted above, these methods are useful for enzyme activity measurements and can be used to test phosphorylation (or dephosphorylation) activity for multiple different enzymes and substrates under a plurality of different reaction conditions.

VI. Consumer Diagnostics

In certain aspects, the invention employs real-time single-molecule enzymatic reactions for institutional and consumer home diagnostic devices for the purpose of health monitoring. Although enzymatic endpoint assays are widely used, the present invention is capable of measuring enzymatic reactions in real time, which can characterize many aspects of the reaction that are impossible to analyze using an ordinary endpoint assay, such as variations in rates of substrate consumption and/or product formation during the course of the reaction, as well as the actual time at which the reaction is complete.

In certain preferred embodiments, the enzymatic reactions are carried out on a substrate upon which single enzymes are immobilized. The single enzymes may be immobilized during manufacturing of the substrate, or they may originate from a sample introduced to the substrate. Such a sample can be a biological sample collected from an organism, e.g., human patient, or can be an environmental sample, e.g., a water, soil, or air sample. A sample to be analyzed on the substrate may be introduced directly or may be processed (e.g., by purification, concentration, etc.) prior to analysis.

Immobilization of the enzyme can occur through any means that does not interfere with the reaction to be monitored. For example, in some preferred embodiments, antibodies specific for particular enzymes of interest are used to bind and immobilize the enzymes to particular locations on the substrate in a way that does not block the catalytic site of the enzyme. This method of immobilization is especially useful where the enzymes are being collected from a sample to be applied to the substrate.

A single substrate may contain multiple binding sites for a single enzyme of interest and/or may contain different binding sites for different enzymes of interest. In preferred embodiments, a substrate comprises at least one or more optical confinements within which a single enzyme of interest is immobilized. In more preferred embodiments, a substrate comprises an array of optical confinements. Such optical confinements may comprise film waveguides, channel waveguides, TIRF substrates, and/or zero-mode waveguides (ZMWs), as described elsewhere herein and in, e.g., U.S. Pat. Nos. 7,313,308 and 7,292,742, incorporated herein by reference in their entireties for all purposes. Typically, the reactions are monitored by optical methods. In certain aspects, simple diagnostic tests such as glucose monitoring or pregnancy tests may be carried out by the methods of the invention. In other aspects, the invention addresses more complex assays such as profiling enzyme panels, complex metabolites, or metabolic pathways.

In some embodiments, rows of optical confinements (e.g., zero mode waveguides) on a substrate are pre-exposed to activated antibodies that are specific for enzymes to be monitored. All antibodies on a substrate can be specific for the same enzyme, or the set of antibodies on a substrate may include antibodies specific for different enzymes. For example, selected rows can be separately addressed with a different antibody via microfluidic channels and the antibody is affixed within the optical confinements, preferably with only a single antibody within any single confinement to promote subsequent immobilization of a single enzyme within the confinement. In this manner, a substrate is prepared comprising multiple rows of confinements, each containing antibodies for a single enzyme of interest. The chip is then preserved and shipped to the consumer, medical institution, or other laboratory. A sample will be collected, e.g., blood or other body fluids, such as sweat, urine, saliva, spinal fluid, semen, synovial fluid, amniotic fluid, etc. by the methods described in the art. The methods typically require only minute quantities of the sample. In some cases, the collection may be performed by a consumer in their home, and in other cases the collection should be performed by a trained technician, e.g., phlebotomist. In some cases, the sample must be processed prior to analysis on the substrate, e.g., to concentrate the sample. Further, the biological samples can be prepared to reduce any potential interference with the detection method, e.g., to minimize colorimetric interference when fluorescent labels are used.

The substrate is exposed to the sample in a device and the bound antibodies capture the enzymes present in the sample to which they are specific. The substrate is optionally washed to remove unbound components of the sample and/or to introduce a buffer solution appropriate for the enzymatic reaction (s). Thereafter, enzymatic reactions are carried out, such as monitoring liver or blood enzyme panels.

In certain embodiments, enzyme assays are carried out on the substrate using fluorescently conjugated metabolites that fluoresce when cleaved or modified. Such substrates include 4-methyl coumarin, o- and p-nitrophenolic compounds, etc. The device is illuminated by lasers or LEDs and the increase or decrease in fluorescence is read versus time and converted to a rate. Alternative detection methods can include FRET pairs that will unfold upon binding and thus emit fluorescence. Such devices can be used to determine common microbial infections and antibodies generated via exposure to specific diseases. The method can also be used to measure metabolites and metabolic cascades.

Further, a diagnostic kit is provided for preparing a set of enzyme-mediated analytical reactions in accordance with the methods provided above. Such a kit preferably includes a substrate comprising an array of optical confinements containing antibodies specific for a molecule of interest in a sample, e.g., an enzyme to be monitored. Preferably, the substrate comprises subsets of optical confinements, each subset containing a particular antibody of interest, such that the array contains subsets of different antibodies to capture a set of molecules of interest from a sample. In preferred embodiments, such a kit also contains instructions for collecting a particular type of biological sample and introducing it onto the substrate. Optionally, the kit also contains a protocol for executing and monitoring the enzyme-mediated analytical reactions, as well as Low to interpret the data generated therefrom.

Advantages of the methods and devices include the following. Diagnostic assays can be multiplexed in laboratories, a doctor's office, or at home using minute amounts of bodily fluids. The actual rates of a reaction of interest are measured rather than endpoints, thereby inherently providing a more accurate measure of enzyme activity. Finally, the system is capable of measuring metabolic cascades in addition to single reactions.

VII. Detection Strategies

The present invention provides various methods for detection of components of various analytical reactions. In certain aspects, one or more components of an analytical reaction comprise detectable labels, e.g., that serve to signal a binding, incorporation, translocation, dissociation, or other catalytic event. Such labels can be detectable moieties known in the art including, but not limited to, chromophores (e.g., fluorophores and other dyes), quantum dots, non-fluorescent tags (e.g., surface enhanced Raman scattering (SERS) particles), scattering metallic nanoparticles (e.g., gold or silver), combinations of chromophores (e.g., FRET labels on a single or multiple components), intrinsic fluorescence, and the like. A variety of detectable labels have been developed in the art, including those described in U.S. Pat. Nos. 6,399,335, 5,866, 366, 7,476,503, and 4,981,977; U.S. Patent Pub. No. 2003/0124576; U.S. Ser. No. 61/164,567; WO 01/16375; Mujumdar, et al Bioconjugate Chem. 4(2):105-111, 1993; Ernst, et al, Cytometry 10:3-10, 1989; Mujumdar, et al, Cytometry 10:1119, 1989; Southwick, et al, Cytometry 11:418-430, 1990; Hung, et al, Anal. Biochem. 243(1):15-27, 1996; Nucleic Acids Res. 20(10:2803-2812, 1992; and Mujumdar, et al, Bioconjugate Chem. 7:356-362, 1996; Intrinsic Fluorescence of Proteins, vol. 6, publisher: Springer US, ©2001; Kronman, M. J. and Holmes, L. G. (2008) Photochem and Photobio 14(2): 113-134; Yanushevich, Y. G., et al. (2003) Russian J. Bioorganic Chem 29(4) 325-329; and Ray, K., et al. (2008) J. Phys. Chem. C 112(46): 17957-17963, all of which are incorporated herein by reference in their entireties for all purposes. Many such labeling groups are commercially available, e.g., from the Amersham Biosciences division of GE Healthcare, and Molecular Protes/Invitrogen Inc. (Carlsbad, Calif.), and are described in 'The Handbook—A Guide to Fluorescent Probes and Labeling Technologies, Tenth Edition' (2005) (available from Invitrogen, Inc./Molecular Probes and incorporated herein in its entirety for all purposes). Further, a combination of the labeling strategies described herein and known in the art for labeling reaction components can be used.

In certain embodiments, a detectable label may be located on a first binding partner such that a signal emitted from the label is altered upon binding to a second binding partner. For example, the label may be repositioned within the binding partner into or out of a hydrophobic binding pocket to cause a change in the signal emitted, e.g., wavelength, intensity, etc. Such a change in signal and the time of such a change is indicative of a functional interaction between binding partners. In some embodiments a detectable label is linked to an immobilized binding partner such that a conformational change that occurs within the immobilized binding partner upon binding to a non-immobilized binding partner causes a change in a signal emitted from the detectable label. Alternatively or in addition, a detectable label can be linked to a non-immobilized binding partner such that a conformational change that occurs within the non-immobilized binding partner upon binding to a immobilized binding partner causes a change in a signal emitted from the detectable label. This labeling strategy would provide a means of detecting the non-immobilized binding partner both before and after binding, thereby distinguishing between entry of the non-immobilized binding partner into the reaction site absent binding, and actual binding of the non-immobilized binding partner to the immobilized binding partner.

With regards to intrinsic fluorescence, the fluorescence of a folded protein is a mixture of the fluorescence from individual aromatic residues, and certain binding events can alter the intrinsic fluorescent of a binding partner, either in intensity or spectral characteristics (e.g., wavelength). For example, most of the intrinsic fluorescence emissions of a folded protein are due to excitation of tryptophan residues, with some emissions due to tyrosine, phenylalanine, and di-suifide bonds, For example, tryptophan typically has a wavelength of maximum absorption of 280 nm and an emission peak that is solvatochromic, ranging from ca. 300-350 nm, depending on the polarity of the local environment (see, e.g., Intrinsic Fluorescence of Proteins and Peptides at dwb[dot]unl[dot]edu/Teacher/ NSF/C08/C08/Links/pps99[dot]cryst[dot]bbk [dot] uk/projects/gmocz/fluor[dot]htm. Hence, protein fluorescence may be used as a diagnostic of the conformational state of a protein (see, e.g., Vivian, et al. (2001) Biophys.J. 80(5):2093-109, incorporated herein by reference in its entirety for all purposes), and has been used to distinguish between specific and non-specific binding events in bulk reactions (see, e.g., Bodenreider, et al. (2009) Anal. Biochem. 395:195-204, incorporated herein by reference in its entirety for all purposes). Furthermore, tryptophan fluorescence is strongly influenced by the proximity of other residues, e.g. nearby protonated groups such as Asp or Glu can cause quenching of Trp fluorescence. Also, energy transfer between tryptophan and other fluorescent amino acids is possible, which would affect the analysis, especially in cases where the Forster acidic approach is taken. Since tryptophan is a relatively rare amino acid (many proteins contain only one or a few tryptophan residues), tryptophan fluorescence can be a very sensitive measurement of the conformational state of individual tryptophan residues. The advantage compared to extrinsic probes is that the protein itself is not changed. In certain preferred embodiments, the use of intrinsic fluorescence for the study of protein conformation is limited to proteins with few (or perhaps only one) tryptophan residues, since each experiences a different local environment, which gives rise to different emission spectra. In further embodiments, fluorescent tryptophan residues (or other fluorescent amino acids or di-sulfide bonds) can be engineered into a binding partner of interest that does not have intrinsic fluorescence. For example, a fluorescent amino acid can be added to a protein in a location such that any specific interaction causes a detectable change in the intrinsic fluorescence, e.g. sterically within a short distance from a known binding pocket. Methods for protein engineering are widely known and used in the art.

The methods can monitor the intrinsic fluorescence from one or more an immobilized binding partners, one or more non-immobilized binding partners, or a combination thereof. For example, a tryptophan residue within a bound protein that is highly fluorescent in the absence of a ligand may be quenched when the ligand binds to the protein, and therefore detection of quenching of the intrinsic fluorescence of the protein is indicative of binding of the ligand. Further, a plurality of different immobilized binding partners are present in an arrayed format and are exposed to a particular non-immobilized binding partner of interest. In some cases, the location of each type of immobilized binding partner is known such that a binding event at a given location can be attributed to binding of a non-immobilized binding partner with an immobilized binding partner known to be at that location. In other cases, the different immobilized binding partners are distributed randomly over the array and each has a detectably different response (change in fluorescence) to binding. Therefore, the type of response detected at a given location is indicative of the type of immobilized binding partner present. In still other cases, the different immobilized binding partners are distributed randomly over the array and each has a detectably different fluorescence in the absence of binding. Therefore, the type of immobilized binding partner present at a given location is determined prior to addition of the non-immobilized binding partner(s).

In yet further embodiments, a mixture of non-immobilized small molecule/peptide or other binding partners can be applied to an array having a given binding partner of interest (or a set of different binding partners of interest) immobilized at a plurality of reaction sites, e.g., ZMWs, nanoholes, etc. For example, the intrinsic fluorescence of the immobilized binding partner(s) at the plurality of reaction sites can be monitored to detect binding of one of the non-immobilized binding partners. Binding is detected as an alteration in the fluorescence of the immobilized binding partner. In some cases, the identity of the non-immobilized binding partner bound to the immobilized binding partner can be determined by the type or extent of alteration of the intrinsic fluorescence. For example, each non-immobilized binding partner can have a detectably different effect on the intrinsic fluorescence of the immobilized binding partner. Alternatively or in addition, the non-immobilized binding partners can emit detectably different signals that distinguish them from one another, and such signals can be related to their own intrinsic fluorescence, or can be emitted from labels bound to the non-immobilized binding partners, e.g., different fluorescent dyes. In certain embodiments in which a mixture of non-immobilized binding partners is exposed to an array of immobilized binding partners, deconvolution from a particular array to identify a specific non-immobilized binding partner bound to a particular immobilized binding partner can be achieved via combinatorial pooling strategies, e.g., as described in Wilson-Lingardo, et al. (1996) J. Med. Chem. 39(14):2720-6, incorporated herein by reference in its entirety for all purposes.

In certain embodiments, detectable labels undergo Förster resonance energy transfer (FRET), and such labels are termed "FRET labels" herein. FRET labels typically comprise at least two chromophores that engage in FRET such that at least a portion of the energy absorbed by at least one "donor chromophore" is transferred to at least one "acceptor chromophore," which emits at least a portion of the transferred energy as a detectable signal contributing to an emission spectrum. In some embodiments, the donor and acceptor reside on a single molecule that undergoes a conformational change that affects the emitted signal, e.g., by varying the distance between them. For example, both donor and acceptor can reside on an immobilized binding partner that undergoes a conformational change upon binding to a non-immobilized binding partner. A change in spectral output is indicative of a binding event, and the type, magnitude, and duration of the change can be used to determine various characteristics of the binding (e.g., affinity, association/dissociation rate, etc.). Alternatively, the donor and acceptor can reside on different molecules that, during the course of a reaction (e.g., during incorporation of an amino acid), bring the chromophores near enough to each other to undergo FRET. Any of a number of fluorophore combinations can be selected for use in the present invention (see for example, Pesce et al., eds, Fluorescence Spectroscopy, Marcel Dekker, New York, 1971; White et al., Fluorescence Analysis: A practical Approach, Marcel Dekker, New York, 1970; Handbook of Fluorescent Probes and Research Chemicals, 6th Ed, Molecular Probes, Inc., Eugene, Oreg., 1996; all of which are incorporated herein by reference in their entireties for all purposes). In general, a preferred donor fluorophore is selected that has a substantial spectral overlap with the acceptor fluorophore. Additional examples of useful FRET labels include, e.g., those described in U.S. Pat. Nos. 5,654,419, 5,688,648, 5,853,992, 5,863,727, 5,945,526, 6,008,373, 6,150,107, 6,177,249, 6,335,440, 6,348,596, 6,479,303, 6,545,164, 6,849,745, 6,696,255, and 6,908,769; Published U.S. Patent Application Nos. 2002/0168641, 2003/0143594, and 2004/0076979; and U.S. Ser. No. 61/164,567, filed Mar. 30, 2009, the disclosures of which are incorporated herein by reference for all purposes. Further, Forster-type resonant energy transfer can also be influenced by metal nanoparticles (see, e.g., Reil, F., et al. (2008) Nano Lett. 8(12); 4128-4133, incorporated herein by reference in its entirety for all purposes).

In certain embodiments, detectable labels are semiconductor nanocrystals such as quantum dots. Quantum dots are particularly significant for optical applications due to their theoretically high quantum yield. High-quality quantum dots are well suited for optical encoding and multiplexing applications due to their broad excitation profiles and narrow/symmetric emission spectra. Quantum dots have been found to have certain beneficial characteristics, including high brightness (owing to the high quantum yield) and high photostability, allowing real-time tracking of molecules and cells over extended periods of time (see, e.g., M. Dahan, et al. (2003) "Diffusion dynamics of glycine receptors revealed by single-quantum dot tracking," Science, vol. 302, pp. 442-445). Quantum dots are known in the art and include those described in U.S. Pat. Nos. 6,207,392, 6,114,038, 6,326,144, 7,192,785, 7,405,434, 7,460,960; Chan et al. (1998) "Quantum Dot Bioconjugates for Ultrasensitive Nonisotopic Detection" Science 281:2016-2018; Bruchez et al. (1998) Science 281:2013-2016. Quantum dots are commercially available from Invitrogen Corporation (Carlsbad, Calif.) and other sources, including Ocean NanoTech (Springdale, Ark.) and eBioscience (San Diego, Calif.). Additional information on preparation, characteristics, and methods for using of various quantum dots can be found in the art, e.g. in Bawendi et al. (1993) J. Am. Chem. Soc. 115:8706; Dabbousi et al. (1997) J. Phys. Chem. B101:9463; Danek et al. (1996) Chem. Mater. 8:173-179; Effros et al. (1996) Physical Review B. 54:4843-4856; Empedocles et al. (1996) Physical Review Letters 77:3873-3876; Goldman et al. (2002) J. Am. Chem. Soc. 124:6378-82; Murakoshi et al. (1998) J. Colloid Interface Sci. 203:225-228; Murray et al. (1993) J. Am. Chem. Soc. 115: 8706-8714; Murray et al. (1996) Science 270: 1355-1338; Nirmal et al. (1996) Nature 383:802-804; Norris et al. (1996) Physical Review B. 53:16338-16346; Pathak et al. (2001) J. Am. Chem. Soc. 123:4103-4; Peng et al. (1997) J. Am. Chem. Soc. 119:7019-7029; Remade et al. (2000) Proc. Natl. Sci. USA 18:553-8; Rodriguez-Viejo et al. (1997) Appl. Phys. Lett. 70:2132-2134; Sacra et al. (1996) J. Chem. Phys. 103: 5236-5245; and Optical Materials and Engineering News (1995) Vol. 5, No. 12, the disclosures of which are incorporated herein by reference in their entireties for all purposes.

In certain embodiments, detectable labels are surface enhanced Raman scattering (SERS) particles. Surface enhanced Raman spectroscopy or surface enhanced Raman scattering, often abbreviated SERS, is a technique that involves the enhancement of Raman scattering by molecules absorbed on a metal surface. The enhancement factor can be as much as 1014-1015, which allows the technique to be sensitive enough to detect single molecules. The use of SERS particles may be particularly beneficial in certain embodiments since at least ten or more types are commercially available (e.g., from Nanopartz (Salt Lake City, Utah), Oxonica (Mountain View, Calif.), and Nanospectra Biosciences (Houston, Tex.)) that have unique spectral emission signatures, thereby allowing great flexibility in differential labeling of multiple components of a reaction mixture. Further, SERS particles also have a high photostability, so are less susceptible to photobleaching or photo-induced damage than certain other detectable labels. Additional information on preparation, characteristics, and methods for using of various SERS particles can be found in the art, e.g. in U.S. Pat. Nos. 7,515,269, 7,511,808, and 7,485,471; PCT Publication Nos. WO/2003/095973 and WO/2008/001978; Nie, S, and Emory, S. R. (1997) Science 275 (5303): 1102-1106; Petrov, D. V. (2007) J. Opt. A: Pure Appl. Opt. 9 S139-S156; Culha, M. et al. (2003) Expert Rev Mol Diagn 3(5): 669-75; Culha, M. et al. (2003) Anal Chem 75(22): 6196-201; and Boncheva, M., et al. (1999) Langmuir 15: 4317, all of which are incorporated herein by reference in their entireties for all purposes.

In some embodiments, surface plasmon resonance (SPR) facilitates detection of unlabeled reactants in real time. SPR-based biosensors can be used in determination of active concentration, screening, and characterization, e.g., in terms of both affinity and kinetics. Surface plasmons, also known as surface plasmon polaritons, are surface electromagnetic waves that propagate in a direction parallel to a metal/dielectric (or metal/vacuum) interface. Since the wave is on the boundary of the metal and the external medium (e.g., air or water), these oscillations are very sensitive to any change of this boundary, such as the adsorption of molecules to the metal surface, and can therefore be used to detect interactions between immobilized and non-immobilized reactants. Methods utilizing plasmon resonance that are applicable to the present invention are provided, e.g., in U.S. Patent Publication No. 20080241866, incorporated herein by reference in its entirety for all purposes.

In further embodiments, combinations of different kinds of labeling groups can be used on different reaction components in a single analytical reaction mixture. For example, chromophore-based labels (e.g., fluorescent dyes) can be linked to a subset of reaction components while SERS labels or quantum dots are linked to a different subset of reaction components. Further, multi-component labels may comprise a combination of different types of labeling groups; for example, a FRET pair can comprise a quantum dot donor and a fluorophore acceptor. The combinations of types of labels used and which reaction components are labeled need only ensure optical distinguishability between reaction components in order to provide the desired reaction characteristic(s) (e.g., sequence of nucleotides incorporated or kinetic characteristics such as rate, processivity, fidelity, etc.) desired by the investigator.

In some embodiments, a detectable label refers to a moiety that is not optically detectable, but still serves to tag and identify a reaction component. For example, in certain embodiments a nucleic acid tag is linked to a reaction component. The nucleic acid tag can be subjected to template-dependent nascent strand synthesis using optically detectable (e.g., fluorescently labeled) nucleotides, such that the sequential incorporation of the nucleotides into the nascent strand is detected in real time to generate a nucleotide sequence for the nascent strand, and, by complementarity, for the nucleic acid tag. Where a nucleic acid tag is specific for a particular reaction component, determination of the nucleotide sequence of the tag identifies the reaction component. As such, although the nucleic acid tag is not optically detectable itself, it can be subjected to a reaction that reveals its identify, and therefore the identity of the reactant at the reaction site. Other such tags include unlabeled tags to which a specific labeled molecule (or molecular complex) will bind and thereby identify, such as unlabeled sugars to which a specific, optically detectable lectin will bind, unlabeled nucleic acids to which a specific, optically detectable complementary nucleic acid will bind, unlabeled antigens to which a specific, optically detectable antibody will bind, and the like.

Detectable labels for use with the compositions, methods, and systems described herein can be attached to various and multiple components of an analytical reaction mixture. For example, one or more may be attached to a polymerase, nucleotide, template, damage-binding agent, component of the damage repair machinery, or a combination thereof. Preferred labels are those that do not substantially impede the continuous and processive nature of an analytical reaction of interest. Methods for detection and analysis of signals emitted from detectable labels are known in the art and certain preferred methods are further described in, e.g., U.S. Pat. Nos.

7,297,532 and 7,329,492; U.S. Patent Publication Nos. 20090024331, 20060228708, 20070036511, 20080080059, 20070188750, 20080277595, and 20070206187; Korlach, et al. (2008) Nucleosides, Nucleotides and Nucleic Acids 27:1072-1083; Eid, et al. (2009) Science 323:133-138; Blanchard (2004) PNAS 101(35):12893-12898; Lundquist, et al. (2008) Optics Letters 33(9):1026-1028; Wang, et al. (2007) Biochemistry 46:10767-10775; Uemura et al. (2008) Nucleic Ac. Res. 36(12):e70; Miyake et al. (2008) Anal. Chem. 80:6018-6022; and Levene, et al. (2003) Science 299:682-686, all of which are incorporated herein by reference for all purposes.

Further, the use of a label that is not constantly present at the reaction site is beneficial in various ways, including mitigation of photo-induced damage that could otherwise negatively impact the ongoing reaction. The term "photo-induced damage" generally refers to any direct or indirect impact of illumination, directed or emitted, on one or more reagents in a reaction resulting in a negative impact upon that reaction. For example, the long-lived triplet-state species of many fluorescent dye molecules exhibits a high degree of chemical reactivity that often results in photobleaching and the production of damaging free radicals and reactive intermediates. For a labeled reaction component that is constantly exchanged during the course of the reaction, e.g., nucleotide that loses its label upon incorporation into a nascent polynucleotide, the problems associated with photobleaching of a stationary label (e.g., one linked to an immobilized polymerase that is continually in the reaction site) would be mitigated. Further, the risk of photo-induced damage to other reaction components that can be immobilized in the reaction site is reduced since the potentially damaging emissions of signal from the label are not constant; that is, such emissions are limited to those periods of time during which the label is present in the reaction site, e.g., during binding until incorporation. Other methods for mitigating photo-induced damage that may be combined with the methods, compositions, and systems of the invention are provided, e.g., in U.S. Ser. No. 61/116,048, 61/139,402, 12/413,226, 61/127,435, and 12/367,411; and in U.S. Patent Pub. No. 20070128133.

VIII. Optical Confinements

In certain aspects, the methods provide a means for studying analytical reactions in vitro by immobilizing at least one component of an analytical reaction in an optical confinement, labeling at least one other component, and detecting signals from the optical confinement during the reaction in real time. An optical confinement is preferentially configured to provide tight optical confinement so only a small volume of the reaction mixture is observable, i.e., signals can only be detected from a small volume of the reaction mixture. In preferred embodiments, optical confinements contain a single analytical reaction to be monitored, e.g., a single immobilized molecule or molecular complex. For example, the practitioner of the methods herein can observe the binding of one protein to one ligand, the synthesis of a nascent nucleotide by a single polymerase enzyme processing a single template nucleic acid, or the phosphorylation of a single molecule. In certain embodiments, optical confinement technologies include zero mode waveguides (ZMWs), total internal reflection microscopy (TIRF), and/or optical waveguides (planar or otherwise configured). For example, in embodiments in which excitation illumination is used to excite chromophore-containing labels, the tight optical confinement allows only a small volume of the reaction mixture to be illuminated, and therefore limits excitation to only those chromophores within that small volume. As such, only the chromophores present in the small illuminated volume are excited and emit signals that are detectable by the optical system. This feature of the invention is useful for reducing the background signal from freely diffusing detectably labeled components in the reaction mixture, thereby enabling the use of high concentrations (e.g., physiological concentrations) of these reagents. Some such optical confinements and methods of manufacture and use thereof are described at length in, e.g., U.S. Pat. Nos. 7,302,146, 7,476,503, 7,313,308, 7,315,019, 7,170,050, 6,917,726, 7,013,054, 7,181,122, and 7,292,742; U.S. Patent Publication Nos. 20080128627, 20080152281, and 200801552280; and U.S. Ser. No. 11/981,740, all of which are incorporated herein by reference in their entireties for all purposes.

Providing such individually resolvable configurations can be accomplished through a number of mechanisms, and typically involves immobilization of at least one component of an analytical reaction at a reaction site. For example, by providing a dilute solution of complexes on a substrate surface suited for immobilization, one will be able to provide individually optically resolvable complexes. (See, e.g., European Patent No. 1105529 to Balasubramanian, et al., the full disclosure of which is incorporated herein by reference in its entirety for all purposes.) Alternatively, one may provide a low density activated surface to which complexes are coupled. (See, e.g., Published International Patent Application No. WO 2007/041394, the full disclosure of which is incorporated herein by reference in its entirety for all purposes). Such individual complexes may be provided on planar substrates or otherwise incorporated into other structures, e.g., zero mode waveguides or waveguide arrays, to facilitate their observation. In preferred embodiments, a substrate comprises at least one optical confinement in which a molecule or molecular complex is immobilized and monitored. The optical confinement is a structure configured to isolate the immobilized molecule/complex from any other molecule/complex immobilized on the substrate, and in particular to isolate any detectable signals emitted from the optical confinement from any other signals emitted from any other optical confinements on the substrate. Such isolation allows the practitioner of the instant invention to unambiguously assign a detected signal to a single optical confinement on the substrate, and therefore to a single analytical reaction on the substrate.

The immobilization of a component of an analytical reaction can be engineered in various ways. For example, an enzyme (e.g., polymerase, transcriptase, kinase, etc.) may be attached to the substrate at a reaction site. In other embodiments, a substrate in an analytical reaction (for example, a nucleic acid template, e.g., DNA, RNA, or hybrids, analogs, and mimetics thereof, or a target molecule for a kinase) may be attached to the substrate at a reaction site. One skilled in the art will appreciate that there are many ways of immobilizing nucleic acids and proteins into an optical confinement, whether covalently or non-covalently, via a linker moiety, or tethering them to an immobilized moiety. These methods are well known in the field of solid phase synthesis and microarrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, among others. Antibodies that specifically bind to one or more reaction components can also be employed as the binding moieties. In addition, a silyl moiety can be attached to a nucleic acid directly to a substrate such as glass using methods known in the art. In some embodiments, a nucleic acid template is immobilized onto a reaction site (e.g., within an optical confinement) by attaching a primer comprising a complementary region at the reaction site that is capable of hybridizing with the tentplate, thereby immobilizing it in a position suitable for monitoring. In certain embodiments, an enzyme complex is assembled in an optical confinement, e.g., by first immobilizing an enzyme component. In other embodiments, an enzyme complex is assembled in solution prior to immobilization.

Where desired, an enzyme or other protein reaction component to be immobilized may be modified to contain one or more epitopes such as Myc, HA (derived from influenza virus hemagglutinin), poly-histadines, and/or FLAG, for which specific antibodies are available commercially. In addition, proteins can be modified to contain heterologous domains such as glutathione S-transferase (GST), maltose-binding protein (MBP), specific binding peptide regions (see e.g., U.S. Pat. Nos. 5,723,584, 5,874,239 and 5,932,433), or the Fc portion of an immunoglobulin. The respective binding agents for these domains, namely glutathione, maltose, and antibodies directed to the Fc portion of an immunoglobulin, are available and can be used to coat the surface of an optical confinement of the present invention.

The binding moieties or agents of the reaction components they immobilize can be applied to the support by conventional chemical techniques which are well known in the art. In general, these procedures can involve standard chemical surface modifications of a support, incubation of the support at different temperature levels in different media comprising the binding moieties or agents, and possible subsequent steps of washing and cleaning.

In some embodiments, a substrate comprising an array of reaction sites is used to monitor multiple biological reactions, each taking place at a single one of the reaction sites. Various means of loading multiple biological reactions onto an arrayed substrate are known to those of ordinary skill in the art and are described further, e.g., in U.S. Ser. No. 61/072, 641, incorporated herein by reference in its entirety for all purposes. For example, basic approaches include: creating a single binding site for a reaction component at the reaction site; removing excess binding sites at the reaction site via catalytic or secondary binding methods; adjusting the size or charge of the reaction component to be immobilized; packaging or binding the reaction component within (or on) a particle (e.g., within a viral capsid), where a single such particle fits into the relevant reaction site (due to size or charge of the particle and/or observation volume); using non-diffusion limited loading; controllably loading the reaction component (e.g., using microfluidic or optical or electrical control); sizing or selecting charges in the reaction sites/observation volumes (e.g., the sizes of optical confinements in an array) to control which reaction components will fit (spatially or electrostatically) into which reaction sites/observation volumes; iterative loading of reaction components, e.g., by masking active sites between loading cycles; enriching the activity of the reaction components that are loaded; using self-assembling nucleic acids to sterically control loading; adjusting the size of the reaction site/observation volume; and many others. Such methods and compositions provide for the possibility of completely loading single-molecule array reaction sites (instead of about 30% of such sites as occurs in "Poisson limited" loading methods) with single reaction components (e.g., molecular complexes).

The optical confinements can be further tailored in various ways for optimal confinement of an analytical reaction of interest. In particular, the size, shape, and composition of the optical confinement can be specifically designed for containment of a given enzyme complex and for the particular label and illumination scheme used.

IX. Systems

The invention also provides systems that are used in conjunction with the compositions and methods of the invention in order to provide for real-time single-molecule detection of analytical reactions. In particular, such systems typically include the reagent systems described herein, in conjunction with an analytical system, e.g., for detecting data from those reagent systems. In certain preferred embodiments, analytical reactions are monitored using an optical system capable of detecting and/or monitoring interactions between reactants at the single-molecule level. For example, such an optical system can achieve these functions by first generating and transmitting an incident wavelength to the reactants, followed by collecting and analyzing the optical signals from the reactants. Such systems typically employ an optical train that directs signals from the reactions to a detector, and in certain embodiments in which a plurality of reactions is disposed on a solid surface, such systems typically direct signals from the solid surface (e.g., array of confinements) onto different locations of an array-based detector to simultaneously detect multiple different optical signals from each of multiple different reactions. In particular, the optical trains typically include optical gratings or wedge prisms to simultaneously direct and separate signals having differing spectral characteristics from each confinement in an array to different locations on an array based detector, e.g., a CCD, and may also comprise additional optical transmission elements and optical reflection elements.

An optical system applicable for use with the present invention preferably comprises at leas an excitation source and a photon detector. The excitation source generates and transmits incident light used to optically excite the reactants in the reaction. Depending on the intended application, the source of the incident light can be a laser, laser diode, a light-emitting diode (LED), a ultra-violet light bulb, and/or a white light source. Further, the excitation light may be evanescent light, e.g., as in total internal reflection microscopy, certain types of waveguides that carry light to a reaction site (see, e.g., U.S. Application Pub. Nos. 20080128627, 20080152281, and 200801552280), or zero mode waveguides, described below. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously (e.g., multiple types of differentially labeled reaction components). A wide variety of photon detectors or detector arrays are available in the art. Representative detectors include but are not limited to an optical reader, a high-efficiency photon detection system, a photodiode (e.g. avalanche photo diodes (APD)), a camera, a charge-coupled device (CCD), an electron-multiplying charge-coupled device (EMCCD), an intensified charge coupled device (ICCD), and a confocal microscope equipped with any of the foregoing detectors. For example, in some embodiments an optical train includes a fluorescence microscope capable of resolving fluorescent signals from individual sequencing complexes. Where desired, the subject arrays of optical confinements contain various alignment aides or keys to facilitate a proper spatial placement of the optical confinement and the excitation sources, the photon detectors, or the optical train as described below.

The subject optical system may also include an optical train whose function can be manifold and may comprise one or more optical transmission or reflection elements. Such optical trains preferably encompass a variety of optical devices that channel light from one location to another in either an altered or unaltered state. First, the optical train collects and/or directs the incident wavelength to the reaction site (e.g., optical confinement). Second, it transmits and/or directs the optical signals emitted from the reactants to the photon detector. Third, it may select and/or modify the optical properties of the incident wavelengths or the emitted wavelengths from the reactants. Illustrative examples of such optical transmission or reflection elements are diffraction gratings, arrayed waveguide gratings (AWG), optical fibers, optical switches, mirrors (including dichroic mirrors), lenses (including microlenses, nanolenses, objective lenses, imaging lenses, and the like), collimators, optical attenuators, filters (e.g., polarization or dichroic filters), prisms, wavelength filters (low-pass, band-pass, or high-pass), planar waveguides, wave-plates, delay lines, and any other devices that guide the transmission of light through proper refractive indices and geometries. One example of a particularly preferred optical train is described in U.S. Patent Pub. No. 20070036511, filed Aug. 11, 2005, and incorporated by reference herein in its entirety for all purposes.

In a preferred embodiment, a reaction site (e.g., optical confinement) containing a reaction of interest is operatively coupled to a photon detector. The reaction site and the respective detector can be spatially aligned (e.g., 1:1 mapping) to permit an efficient collection of optical signals from the reactants. In certain preferred embodiments, a reaction substrate is disposed upon a translation stage, which is typically coupled to appropriate robotics to provide lateral translation of the substrate in two dimensions over a fixed optical train. Alternative embodiments could couple the translation system to the optical train to move that aspect of the system relative to the substrate. For example, a translation stage provides a means of removing a reaction substrate (or a portion thereof) out of the path of illumination to create a non-illuminated period for the reaction substrate (or a portion thereof), and returning the substrate at a later time to initiate a subsequent illuminated period. An exemplary embodiment is provided in U.S. Patent Pub. No. 20070161017, filed Dec. 1, 2006.

In particularly preferred aspects, such systems include arrays of reaction regions, e.g., zero mode waveguide arrays, that are illuminated by the system, in order to detect signals (e.g., fluorescent signals) therefrom, that are in conjunction with analytical reactions being carried out within each reaction region. Each individual reaction region can be operatively coupled to a respective microlens or a nanolens, preferably spatially aligned to optimize the signal collection efficiency. Alternatively, a combination of an objective lens, a spectral filter set or prism for resolving signals of different wavelengths, and an imaging lens can be used in an optical train, to direct optical signals from each confinement to an array detector, e.g., a CCD, and concurrently separate signals from each different confinement into multiple constituent signal elements, e.g., different wavelength spectra, that correspond to different reaction events occurring within each confinement. In preferred embodiments, the setup further comprises means to control illumination of each confinement, and such means may be a feature of the optical system or may be found elsewhere is the system, e.g., as a mask positioned over an array of confinements. Detailed descriptions of such optical systems are provided, e.g., in U.S. Patent Pub. No. 20060063264, filed Sep. 16, 2005, which is incorporated herein by reference in its entirety for all purposes.

The systems of the invention also typically include information processors or computers operably coupled to the detection portions of the systems, in order to store the signal data obtained front the detector(s) on a computer readable medium, e.g., hard disk, CD, DVD or other optical medium, flash memory device, or the like. For purposes of this aspect of the invention, such operable connection provides for the electronic transfer of data from the detection system to the processor for subsequent analysis and conversion. Operable connections may be accomplished through any of a variety of well known computer networking or connecting methods, e.g., Firewire®, USB connections, wireless connections, WAN or LAN connections, or other connections that preferably include high data transfer rates. The computers also typically include software that analyzes the raw signal data, identifies signal pulses that are likely associated with incorporation events, and identifies bases incorporated during the sequencing reaction, in order to convert or transform the raw signal data into user interpretable sequence data (see, e.g., Published U.S. Patent Application No. 2009-0024331, the full disclosure of which is incorporated herein by reference in its entirety for all purposes).

Exemplary systems are described in detail in, e.g., U.S. patent application Ser. No. 11/901,273, filed Sep. 14, 2007 and U.S. patent application Ser. No. 12/134,186, filed Jun. 5, 2008, the full disclosures of which are incorporated herein by reference in their entirety for all purposes.

Further, the invention provides data processing systems for transforming raw data generated in an analytical reaction into analytical data that provides a measure of one or more aspects of the reaction under investigation, e.g., transforming signals from a sequencing-by-synthesis reaction into nucleic acid sequence read data, which can then be transformed into consensus sequence data. In certain embodiments, the data processing systems include machines for generating nucleic acid sequence read data by polymerase-mediated processing of a template nucleic acid molecule (e.g., DNA or RNA). The nucleic acid sequence read data generated is representative of the nucleic acid sequence of the nascent polynucleotide synthesized by a polymerase translocating along a nucleic acid template only to the extent that a given sequencing technology is able to generate such data, and so may not be identical to the actual sequence of the nascent polynucleotide molecule. For example, it may contain a deletion or a different nucleotide at a given position as compared to the actual sequence of the polynucleotide, e.g., when a nucleotide incorporation is missed or incorrectly determined, respectively. As such, it is beneficial to generate redundant nucleic acid sequence read data, and to transform the redundant nucleic acid sequence read data into consensus nucleic acid sequence data that is generally more representative of the actual sequence of the polynucleotide molecule than nucleic acid sequence read data from a single read of the nucleic acid molecule. Redundant nucleic acid sequence read data comprises multiple reads, each of which includes at least a portion of nucleic acid sequence read that overlaps with at least a portion of at least one other of the multiple nucleic acid sequence reads. As such, the multiple reads need not all overlap with one another, and a first subset may overlap for a different portion of the nucleic acid sequence than does a second subset. Such redundant sequence read data can be generated by various methods, including repeated synthesis of nascent polynucleotides from a single nucleic acid template, synthesis of polynucleotides from multiple identical nucleic acid templates, or a combination thereof.

In another aspect, the data processing systems can include software and algorithm implementations provided herein, e.g. those configured to transform redundant nucleic acid sequence read data into consensus nucleic acid sequence data, which, as noted above, is generally more representative of the actual sequence of the nascent polynucleotide molecule than nucleic acid sequence read data from a single read of a single nucleic acid molecule. Further, the transformation of the redundant nucleic acid sequence read data into consensus nucleic acid sequence data identifies and negates some or all of the single-read variation between the multiple reads in the redundant nucleic acid sequence read data. As such, the transformation provides a representation of the actual nucleic acid sequence of the nascent polynucleotide complementary to the nucleic acid template that is more accurate than a representation based on a single read.

Various methods and algorithms for data transformation employ data analysis techniques that are familiar in a number of technical fields, and are generally referred to herein as statistical analysis. For clarity of description, details of known techniques are not provided herein. These techniques are discussed in a number of available reference works, such as those provided in U.S. Patent Publication No. 20090024331 and U.S. Ser. No. 61/116,439, filed Nov. 20, 2008, the disclosures of which are incorporated herein by reference in their entireties for all purposes.

The software and algorithm implementations provided herein are preferably machine-implemented methods, e.g., carried out on a machine comprising computer-readable medium configured to carry out various aspects of the methods herein. For example, the computer-readable medium preferably comprises at least one or more of the following: a) a user interface; b) memory for storing raw analytical reaction data (e.g., detected signals, time-based characteristics, information on reaction conditions, information on reaction components, etc.); c) memory storing software-implemented instructions for carrying out the algorithms for transforming the raw analytical reaction data into transformed data that characterizes one or more aspects of the reaction (e.g., rate, consensus sequence data, etc.); d) a processor for executing the instructions; e) software for recording the results of the transformation into memory; and f) memory for recordation and storage of the transformed data. In preferred embodiments, the user interface is used by the practitioner to manage various aspects of the machine, e.g., to direct the machine to carry out the various steps in the transformation of raw data into transformed data, recordation of the results of the transformation, and management of the transformed data stored in memory.

As such, in preferred embodiments, the methods further comprise a transformation of the computer-readable medium by recordation of the raw analytical reaction data and/or the transformed data generated by the methods. Further, the computer-readable medium may comprise software for providing a graphical representation of the raw analytical reaction data and/or the transformed data, and the graphical representation may be provided, e.g., in soft-copy (e.g., on an electronic display) and/or hard-copy (e.g., on a print-out) form.

The invention also provides a computer program product comprising a computer-readable medium having a computer-readable program code embodied therein, the computer readable program code adapted to implement one or more of the methods described herein, and optionally also providing storage for the results of the methods of the invention. In certain preferred embodiments, the computer program product comprises the computer-readable medium described above.

In another aspect, the invention provides data processing systems for transforming raw analytical reaction data from one or more analytical reactions into transformed data representative of a particular characteristic of an analytical reaction, e.g., an actual sequence of one or more template nucleic acids analyzed a rate of an enzyme-mediated reaction, an identity of a kinase target molecule, and the like. Such data processing systems typically comprise a computer processor for processing the raw data according to the steps and methods described herein, and computer usable medium for storage of the raw data and/or the results of one or more steps of the transformation, such as the computer-readable medium described above.

Figure 6:
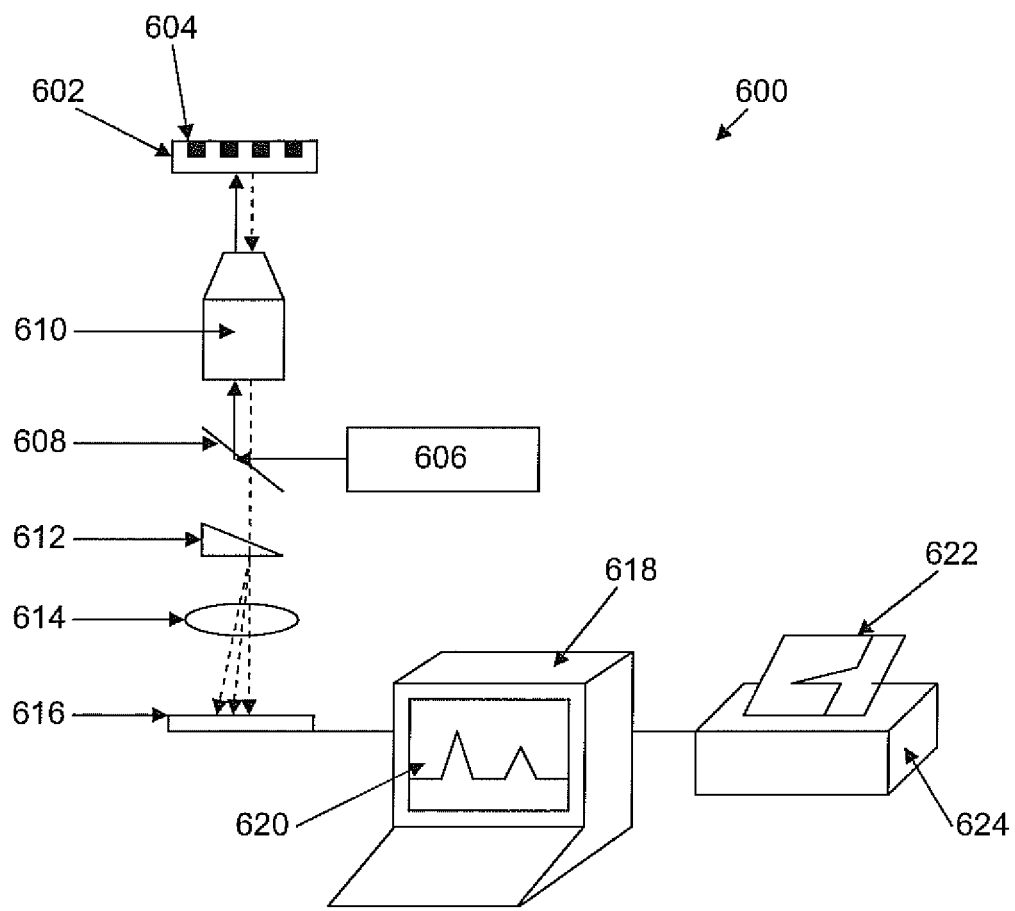
FIG. 6 schematically illustrates one embodiment of a system for use with the methods, devices, and systems of the invention.

As shown in FIG. 6, the system 600 includes a substrate 602 that includes a plurality of discrete sources of chromophore emission signals, e.g., an array of zero mode waveguides 604. An excitation illumination source, e.g., laser 606, is provided in the system and is positioned to direct excitation radiation at the various signal sources. This is typically done by directing excitation radiation at or through appropriate optical components, e.g., dichroic 608 and objective lens 610, that direct the excitation radiation at the substrate 602, and particularly the signal sources 604. Emitted signals from the sources 604 are then collected by the optical components, e.g., objective 610, and passed through additional optical elements, e.g., dichroic 608, prism 612 and lens 614, until they are directed to and impinge upon an optical detection system, e.g., detector array 616. The signals are then detected by detector array 616, and the data from that detection is transmitted to an appropriate data processing system, e.g., computer 618, where the data is subjected to interpretation, analysis, and ultimately presented in a user ready format, e.g., on display 620, or printout 622, from printer 624. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119, and U.S. patent application Ser. No. 11/901,273, all of which are incorporated herein by reference in their entireties for all purposes.)

It is to be understood that the above description is intended to be illustrative and not restrictive. It readily should be apparent to one skilled in the art that various embodiments and modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated herein by reference in its entirety for all purposes.

What is claimed is:

1. A method of determining a consensus binding site of a binding partner on a random array of optically resolvable polymer molecules, said determining comprising:
(i) providing optically resolvable reaction sites arrayed on a substrate and synthesizing a plurality of different polymer molecules wherein a single polymer molecule is synthesized at each of the optically resolvable reaction sites, wherein the synthesizing comprises exposing the reaction sites to a reaction mixture comprising a plurality of different types of monomers, wherein each type is linked to a detectably distinct label, under conditions that promote enzyme-mediated incorporation of the monomers into the single polymer molecule, and further wherein the synthesizing is performed in the presence of the binding partner, thereby generating a random array of optically resolvable polymer molecules, and further wherein the different polymer molecules are polynucleotides or polypeptides and the binding partner is selected from the group consisting of a protein, a carbohydrate, or a nucleic acid;

(ii) monitoring each of the reaction sites during said synthesizing to generate a set of time sequences of incorporations of the monomers at each of the reaction sites, thereby determining the sequences of the optically resolvable polymer molecules and mapping their locations on the substrate, wherein the monitoring comprises detecting the detectably distinct label;

(iii) monitoring each of the reaction sites during said synthesizing to detect binding of the binding partner to a subset of the optically resolvable polymer molecules at the optically resolvable reaction sites on the substrate; and (iv) using the sequences of the optically resolvable polymer molecules determined in (ii), identifying a common monomer sequence in the sequences of the subset of the optically resolvable polymer molecules to which the binding partner bound in (iii), wherein the common monomer sequence is the consensus binding site for the binding partner, thereby identifying the consensus binding site of the binding partner.

2. The method of claim 1, wherein the single polymer molecules are polypeptides.

3. The method of claim 1, wherein the single polymer molecules are nucleic acids and the binding partner is selected from the group consisting of a transcription factor, a histone, an antibody, an RNA, an enzyme, and a nucleic acid binding protein.

4. The method of claim 1, wherein the binding partner comprises a detectable label.

5. The method of claim 4, wherein the detectable label on the binding partner comprises a fluorophore.

6. The method of claim 1, wherein the binding partner undergoes a conformational change upon binding that changes its intrinsic fluorescence.

7. The method of claim 1, wherein the reaction mixture further comprises an agent that alters binding between the common monomer sequence and the binding partner relative to binding in the absence of the agent.

8. The method of claim 1, further comprising monitoring the reaction site under a first set of reaction conditions to detect a first binding result for the binding partner, changing the first set of reaction conditions to a second set of reaction conditions, and monitoring the reaction site under the second set of conditions to detect a second binding result for the binding partner.

9. The method of claim 1, wherein the different polymer molecules are nucleic acid products of template-directed synthesis reactions.

10. The method of claim 9, wherein polymerase enzymes catalyze the template-directed synthesis reactions.

11. The method of claim 1, further comprising immobilizing a plurality of molecular complexes at the reaction sites, wherein the molecular complexes each comprise an enzyme and a nucleic acid template, wherein a plurality of different nucleic acid templates are present in the plurality of molecular complexes, and further wherein the sequence of the nucleic acid template in each of the molecular complexes is unknown during the immobilizing, wherein the plurality of different polymer molecules is synthesized by the enzyme in the molecular complex.

12. The method of claim 11, wherein the enzyme is a polymerase enzyme, the monomers comprise nucleotides, and the polymer molecule is a polynucleotide complementary to the nucleic acid template.

13. The method of claim 11, wherein the enzyme is a ribosome, the monomers comprise amino acids, and the polymer is a polypeptide encoded by the nucleic acid template.

14. The method of claim 1, wherein the optically resolvable reaction sites are within optical confinements.

15. The method of claim 14, wherein the optical confinements are zero mode waveguides.

* * * * *